United States Patent
Blum et al.

(10) Patent No.: US 9,926,292 B2
(45) Date of Patent: Mar. 27, 2018

(54) PYRIDINYL DERIVATIVES, PHARMACEUTICAL COMPOSITIONS AND USES THEREOF

(71) Applicant: Boehringer Ingelheim International GmbH, Ingelheim am Rhein (DE)

(72) Inventors: Andreas Blum, Darmstadt (DE); Cédrickx Godbout, Attenweiler (DE); Joerg P. Hehn, Biberach an der Riss (DE); Stefan Peters, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/588,739

(22) Filed: May 8, 2017

(65) Prior Publication Data

US 2017/0327483 A1 Nov. 16, 2017

(30) Foreign Application Priority Data

May 12, 2016 (EP) ..................................... 16169356

(51) Int. Cl.
- C07D 401/04 (2006.01)
- C07D 405/14 (2006.01)
- C07D 401/14 (2006.01)
- C07D 413/14 (2006.01)
- C07D 417/14 (2006.01)

(52) U.S. Cl.
CPC ......... *C07D 401/04* (2013.01); *C07D 401/14* (2013.01); *C07D 405/14* (2013.01); *C07D 413/14* (2013.01); *C07D 417/14* (2013.01)

(58) Field of Classification Search
CPC ........................... C07D 417/14; C07D 401/14
See application file for complete search history.

(56) References Cited

U.S. PATENT DOCUMENTS

2008/0096892 A1* 4/2008 Chen et al. .......... A61K 31/498
514/249

FOREIGN PATENT DOCUMENTS

| EP | 2695881 A1 | 2/2014 |
| WO | 2017022861 A1 | 2/2017 |

OTHER PUBLICATIONS

Interational Search Report and Written Opinion for PCT/EP20170600890, dated Jun. 6, 2017.
Yamaki, Synthesis and structure activity relationships of carbamimidoylcarbamate derivatives as novel vascular adhesion protein-1 inhibitors, Bioorganic and medicinal Chemistry, 2017, p. 6024-6038.

* cited by examiner

*Primary Examiner* — Alexander R Pagano
*Assistant Examiner* — Ebenezer O Sackey
(74) *Attorney, Agent, or Firm* — Marc Began; David L. Kershner

(57) ABSTRACT

The invention relates to new pyridinyl derivatives of the formula

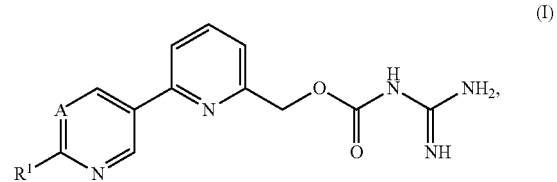

(I)

wherein $R^1$ and A are as defined in the description and claims, to their use as medicaments, to methods for their therapeutic use and to pharmaceutical compositions containing them.

21 Claims, No Drawings

PYRIDINYL DERIVATIVES, PHARMACEUTICAL COMPOSITIONS AND USES THEREOF

FIELD OF THE INVENTION

This invention relates to new compounds, in particular pyridinyl derivatives, to processes for preparing such compounds, to their use as inhibitors of AOC3, to methods for their therapeutic use, in particular in diseases and conditions mediated by the inhibition of AOC3, and to pharmaceutical compositions comprising them.

BACKGROUND OF THE INVENTION

The enzymatic activity of AOC3 (amine oxidase, copper containing 3; vascular adhesion protein 1) has been described already in 1967 as a monoamine oxidase activity in the plasma of chronic liver disease patients (Gressner, A. M. et al., 1982, J. Clin. Chem. Clin. Biochem. 20: 509-514; McEwen, C. M., Jr. et al.,1967, J. Lab Clin. Med. 70: 36-47). AOC3 has two closely homologous genes in the human genome: AOC1 which corresponds to a diamine oxidase (Chassande, O. et al., 1994, J. Biol. Chem. 269: 14484-14489) and AOC2, a SSAO with a specific expression in the retina (Imamura, Y. et al., 1997, Genomics 40: 277-283). AOC4 is a sequence that does not lead to a functional gene product in humans due to an internal stop-codon (Schwelberger, H. G., 2007, J. Neural Transm. 114: 757-762).

The enzyme contains an oxidized 2,4,5-trihydroxy-phenylalaninequinone (TPQ) and a copper ion in the active side. This characteristic catalytic center classifies the semicarbazide-sensitive amine oxidase (SSAO, copper-containing amine:oxygen oxido-reductase (deaminating)): The type II membrane protein belongs to the family of copper containing amine oxidases together with several other diamine and the lysyl oxidases. However the later enzymes can be distinguished from AOC3 in their preference for diamines and the low sensitivity towards semicarbazide inhibition (Dunkel, P. et al., 2008, Curr. Med. Chem. 15: 1827-1839). On the other hand, monoamine oxidases contain the flavin adenine dinucleotide (FAD) cofactor in their reactive center like monoamine oxidase A (MAO-A) and monoamine oxidase B (MAO-B) and follow therefore a different reaction scheme.

AOC3 catalyzes a two-step reaction mechanism for the oxidative deamination of primary aliphatic and aromatic amines. In a first reaction the primary amine forms a Schiff-base with the TPQ aldehyde. This covalent bond is hydrolyzed, releasing the aldehyde product and a substituted TPQ residue in the active site. In the presence of oxygen, TPQ is oxidized under the formation of ammonia and peroxide with the help of the copper ion (Mure, M. et al., 2002, Biochemistry 41: 9269-9278). Several substrates of AOC3 have been described, like the physiological amines methylamine, dopamine, or aminoacetone, whose products of oxidation have been associated to cardiovascular pathologies (Yu, P. H. et al.,1993, Diabetes 42: 594-603). Synthetic amines have been optimized for their turnover by AOC3 like benzylamine derivates (Yraola, F. et al., 2006, J. Med. Chem. 49: 6197-6208), C-Naphthalen-1-methylamine (Marti, L. et al., 2004, J. Med. Chem. 47: 4865-4874) or luciferin derivates (Valley, M. P. et al., 2006, Anal. Biochem. 359: 238-246). The later substrate can be used for the sensitive detection of AOC3 activity in plasma, tissue or for biochemical characterization of the enzyme.

Under pathophysiological conditions of high AOC3 activity the aldehyde products are highly reactive, leading to advanced glycosylation end products (Mathys, K. C. et al., 2002, Biochem. Biophys. Res. Commun. 297: 863-869) which are regarded as markers and drivers of diabetes associated inflammatory mechanisms.

Furthermore, the byproduct hydrogen peroxide is sensed by the tissue as a messenger of inflammation. This reaction product is able to activate the endothelium and is fostering the activation of leukocytes.

The binding and modification of Siglec-10 as a membrane bound substrate provides a mechanistic understanding of how the enzymatic reaction could trigger the leukocyte transmigration through activated endothelia. The binding of Siglec-10 to AOC3 was shown in several adhesion assays and led to increased hydrogen peroxide production (Kivi, E. et al., 2009, Blood 114: 5385-5392). Binding of activated leukocytes to the dimeric, extracellular AOC3 via the Siglec-10 generates a transient association to the activated endothelium. Therefore, the rolling velocity of leukocytes is reduced, which increases the transmigration of leukocytes into the interstitium of inflamed tissues. Further, a conserved RGD-motif on the surface of AOC3 argues for its adhesive role: The deletion of this sequence reduced leukocyte recruitment (Salmi, M. et al., 2000, Circ. Res. 86: 1245-1251), probably via a lack of integrin β1 binding activity (Aspinall, A. I. et al., 2010, Hepatology 51: 2030-2039).

This finding correlates to the phenotype of AOC3 knock out mice, which exert a reduced leukocyte and lymphocyte transmigration capacity (Stolen, C. M. et al., 2005, Immunity. 22: 105-115) into lymphoid organs and adipose tissue (Bour, S. et al., 2009, Am. J. Pathol. 174: 1075-1083).

AOC3 activity can be found in most tissues and is mainly expressed in endothelial cells, smooth muscle cells and adipocytes (Boomsma, F. et al.,2000, Comp Biochem. Physiol C. Toxicol. Pharmacol. 126: 69-78; O'Sullivan, J. et al.,2004, Neurotoxicology 25: 303-315). In humans, in contrast to mice, AOC3 activity is constitutive in the liver sinusoideal endothelial cells (McNab, G. et al., 1996, Gastroenterology 110: 522-528) and mRNA expression is further upregulated under inflammatory conditions in this tissue (Lalor, P. F. et al., 2002, Immunol. Cell Biol. 80: 52-64); Bonder, C. S. et al., 2005, Immunity. 23: 153-163). AOC3 not only exists as a membrane protein, but can also be found as soluble plasma activity probably due to a metalloprotease mediated shedding process (Abella, A. et al., 2004, Diabetologia 47: 429-438); Boomsma, F. et al., 2005, Diabetologia 48: 1002-1007; Stolen, C. M. et al., 2004, Circ. Res. 95: 50-57)). Elevated levels of soluble AOC3 have been observed in diabetes (Li, H. Y. et al., 2009, Clin. Chim. Acta 404: 149-153), obesity (Meszaros, Z. et al., 1999, Metabolism 48: 113-117; Weiss, H. G. et al., 2003, Metabolism 52: 688-692), congestive heart failure (Boomsma, F. et al., 1997, Cardiovasc. Res. 33: 387-391), end-stage renal disease (Kurkijarvi, R. et al., 2001, Eur. J. Immunol. 31: 2876-2884) and inflammatory liver disease (Kurkijarvi, R. et al., 1998, J. Immunol. 161: 1549-1557). For the latter, levels of AOC3 plasma activity have been correlated to liver fibrosis and serve as a predictor in patients with NAFLD (Weston, C. J. et al., 2011, J. Neural Transm. 118: 1055-1064). After transplantation of cirrhotic livers, high AOC3 plasma levels returned to normal values, which argues for the liver as the major source of plasma AOC3 activity under this pathological condition (Boomsma, F. et al., 2003, Biochim. Biophys. Acta 1647: 48-54).

The role of AOC3 in the activation of inflammation via peroxide generation and the recruitment of leukocytes to activated endothelium makes it an attractive target for the treatment of inflammatory components in several diseases. Therefore a variety of small molecular compounds and antibodies have been tested in different disease animal models. Amongst those, the inhibition of AOC3 showed beneficial effects in the models of melanoma and lymphoma cancer (Marttila-Ichihara, F. et al., 2010, J. Immunol. 184: 3164-3173), acute and chronic joint (Tabi, T. et al., 2013, J. Neural Transm. 120: 963-967) or lung (Foot, J. S. et al., 2013, J. Pharmacol. Exp. Ther. 347: 365-374) inflammation, diabetic macular edema (Inoue, T. et al., 2013,Bioorg. Med. Chem. 21: 1219-1233), kidney fibrosis (Wong, M. et al., 2014, Am. J. Physiol Renal Physiol 307: F908-F916), liver allograft rejection (Martelius, T. et al., 2004, Am. J. Pathol. 165: 1993-2001) and non-alcoholic liver disease.

The development of a selective, potent and well tolerated AOC3 inhibitor would therefore be beneficial for the treatment of the respective human diseases.

AOC3 inhibitors are known in the art, for example, the compounds disclosed in EP 2 695 881 corresponding to WO 2012/124696. The pyridinyl derivatives of the present invention may provide several advantages, such as enhanced potency, reduced plasma protein binding, improved CYP (cytochrome P450) enzyme profile and high metabolic stability, high chemical stability, improved tissue distribution, improved side effect profile and/or tolerability and in consequence low toxicity, reduced risk to cause adverse events or undesirable side effects, and enhanced solubility. The pyridinyl derivatives of the present invention exhibit increased selectivity towards AOC1. AOC1 expression and enzymatic activity is mainly found in the gut, placenta and kidney. The enzyme catalyzes the oxidation of primary amines derived from nutrition and protects the individuum from cardiometabolic effects of histamine, putrescine, tryptamine and cadaverine. Inhibition of AOC1 can lead to impaired tolerance to ingested histamine, resulting in increased plasma and tissue histamine-levels which can cause adverse events or undesirable side effects like decreased aterial pressure and compensation by increased heart-rate, tachycardia, headache, flush, urticaria, pruritus, bronchospasm and cardiac arrest (Maintz L. and Novak N. 2007. Am. J. Clin. Nutr. 85:1185-96). The consequence of AOC1 inhibition in combination with histamine intake has been demonstrated in experiments with pigs: After the application of the AOC1-inhibitor aminoguanidine (100 mg/kg) and gavage of histamine (2 mg/kg) animals experienced increased histamine blood levels accompanied with a drop of blood pressure, increased heart rate, flushing, vomiting and death (3 out of 15 animals) (Sattler J. 1988. Agents and Actions, 23: 361-365) under the experimental conditions. Histamine intolerance in humans was associated to mutations in the promoter region of AOC1, leading to reduced mRNA expression and plasma AOC1 activity (Maintz et al. 2011. Allergy 66: 893-902).

AIM OF THE PRESENT INVENTION

The aim of the present invention is to provide new compounds, in particular new pyridinyl derivatives, which are active with regard to AOC3.

A further aim of the present invention is to provide new compounds, in particular new pyridinyl derivatives, which have an inhibitory effect on AOC3 in vitro and/or in vivo and possess suitable pharmacological and pharmacokinetic properties to use them as medicaments.

A further aim of the present invention is to provide effective AOC3 inhibitors, in particular for the treatment of various diseases, for example of NASH (non-alcoholic steatohepatitis), pulmonary fibrosis, retinopathy and nephropathy.

Another aim of the present invention is to provide effective AOC3 inhibitors for the treatment of metabolic disorders such as NASH (non-alcoholic steatohepatitis), pulmonary fibrosis, retinopathy and nephropathy.

A further aim of the present invention is to provide methods for treating a disease or condition mediated by the inhibition of AOC3 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular pyridinyl derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

SUMMARY OF THE INVENTION

Within the scope of the present invention it has now surprisingly been found that the new compounds of general formula (I) as described hereinafter exhibit an inhibiting activity with regard to AOC3.

According to another aspect of the present invention it has been found that the new compounds of general formula (I) as described hereinafter exhibit an inhibiting activity with regard to AOC3.

In a first aspect the present invention provides a compound of general formula

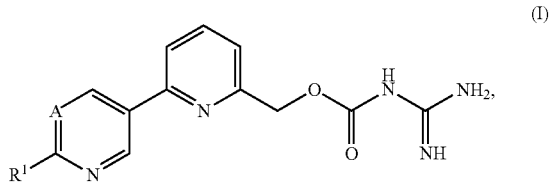

(I)

wherein
A is selected from the group A-G1 consisting of: N and CH;
$R^1$ is selected from the group $R^1$-G1 consisting of:
$C_{1-6}$-alkyl, $C_{3-6}$-cycloalkyl, heterocyclyl, —O—$R^2$, —S—$R^2$, —NH—$R^2$ and —N($R^2$)$_2$,
wherein each $R^2$ is independently selected from the group $R^2$-G1 consisting of $C_{1-6}$-alkyl, $C_{3-6}$-cycloalkyl, heterocyclyl, —($C_{1-2}$-alkyl)-($C_{3-6}$-cycloalkyl), —($C_{1-2}$-alkyl)-heterocyclyl, —($C_{1-2}$-alkyl)-aryl, —($C_{1-2}$-alkyl)-heteroaryl and —($C_{1-2}$-alkyl)-C≡CH;
wherein each heterocyclyl of $R^1$ and $R^2$ is a 4- to 7-membered saturated carbocyclic group, in which 1 or 2 $CH_2$-moieties are independently of each other replaced by an atom or group selected from NH, O, S, —S(=O)—, —S(=O)$_2$— or —C(=O)—; and wherein each aryl is selected from the group consisting of phenyl and naphthyl; and wherein each heteroaryl is a 5- or 6-membered heteroaromatic ring which contains 1, 2 or 3 heteroatoms independently selected from =N—, —NH—, —O— and —S—, wherein in heteroaromatic groups containing a —CH=N— unit, this group is optionally replaced by —NH—C(=O)—; and wherein each alkyl, cycloalkyl, heterocyclyl, aryl or heteroaryl group of $R^1$ and $R^2$ is optionally independently substituted with one or more F, Cl, CN, OH, $C_{1-3}$-alkyl, —O—($C_{1-3}$-alkyl), —C(=O)—($C_{1-3}$-alkyl) and —C(=O)—($C_{3-7}$-cycloalkyl);

wherein each of the above-mentioned alkyl and —O-alkyl groups may be linear or branched and are optionally substituted by one or more F;

a tautomer or stereoisomers thereof, or a salt thereof, or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of AOC3 in a patient in need thereof characterized in that a compound of general formula (I) or a pharmaceutically acceptable salt thereof is administered to the patient.

According to another aspect of the invention, there is provided a method for treating NASH (non-alcoholic steatohepatitis), pulmonary fibrosis, retinopathy or nephropathy in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described above or hereinafter.

According to another aspect of the invention, there is provided a compound of the general formula (I) or a pharmaceutically acceptable salt thereof for use in a therapeutic method as described above or hereinafter.

In a further aspect this invention relates to a method for treating a disease or condition mediated by the inhibition of AOC3 in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of AOC3.

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly A, $R^1$ and $R^2$, are defined as above and hereinafter. If residues, substituents or groups occur several times in a compound, as for example $R^2$, they may have the same or different meanings. Some preferred meanings of individual groups and substituents of the compounds according to the invention will be given hereinafter. Any and each of these definitions may be combined with each other.

A:

A-G1:

The group A is preferably selected from the group A-G1 as defined above.

A-G2:

In another embodiment the group A is selected from the group A-G2 consisting of N.

A-G3:

In another embodiment the group A is selected from the group A-G3 consisting of CH.

$R^1$:

$R^1$-G1:

The group $R^1$ is preferably selected from the group $R^1$-G1 as defined above.

$R^1$-G2:

In one embodiment the group $R^1$ is selected from the group $R^1$-G2 consisting of: $C_{1-4}$-alkyl, $C_{3-5}$-cycloalkyl, heterocyclyl, —O—$R^2$, —S—$R^2$, —NH—$R^2$ and —N($R^2$)$_2$;

wherein each heterocyclyl is a 4- to 6-membered saturated carbocyclic group, in which 1 or 2 $CH_2$-moieties are replaced by a heteroatom selected from NH, O or S; and wherein each alkyl, cycloalkyl or heterocyclyl group is optionally independently substituted with 1 to 5 F and / or 1 to 3 substituents independently selected from the group consisting of Cl, CN, OH, $C_{1-2}$-alkyl, —O—($C_{1-2}$-alkyl), —O(=O)—($C_{1-2}$-alkyl) and —C(=O)—($C_{3-4}$-cycloalkyl).

$R^1$-G3:

In another embodiment the group $R^1$ is selected from the group $R^1$-G3 consisting of: $C_{1-3}$-alkyl, $C_{3-4}$-cycloalkyl, heterocyclyl, —O—$R^2$, —S—$R^2$, —NH—$R^2$ and —N($R^2$)$_2$;

wherein each heterocyclyl is selected from the group consisting of azetidinyl, piperidinyl, piperazinyl, tetrahydrofuranyl, tetrahydropyranyl and morpholinyl; and wherein each alkyl, cycloalkyl or heterocyclyl group is optionally independently substituted with 1 to 3 F and/or one substituent selected from the group consisting of CN, OH, $CH_3$, —O—$CH_3$, —C(=O)—$CH_3$ and —C(=O)-cyclopropyl.

$R^1$-G4:

In another embodiment the group $R^1$ is selected from the group $R^1$-G4 consisting of: $C_{1-2}$-alkyl, $C_{3-4}$-cycloalkyl, heterocyclyl, —O—$R^2$, —NH—$R^2$ and —N($R^2$)$_2$;

wherein each heterocyclyl is selected from the group consisting of azetidinyl, piperidinyl, tetrahydrofuranyl, tetrahydropyranyl and morpholinyl; and wherein each alkyl, cycloalkyl or heterocyclyl group is optionally independently substituted with 1 to 3 F or one substituent selected from the group consisting of CN, OH, $CH_3$, —O—$CH_3$, —C(=O)—$CH_3$ and —C(=O)-cyclopropyl.

$R^1$-G5:

In another embodiment the group $R^1$ is selected from the group $R^1$-G5 consisting of: cyclopropyl, heterocyclyl and —O—$R^2$;
  wherein each heterocyclyl is selected from the group consisting of azetidinyl, piperidinyl, tetrahydrofuranyl, tetrahydropyranyl and morpholinyl; and
  wherein each heterocyclyl group is optionally independently substituted with one substituent selected from the group consisting of F, CN, OH, $CH_3$, —O—$CH_3$.

$R^1$-G6:

In another embodiment the group $R^1$ is selected from the group $R^1$-G6 consisting of:
  a) $CH_3$;
  b) —O—$C_{1-4}$-alkyl optionally substituted with 1-3 F or one —$OCH_3$;
  c) —O—$C_{2-4}$-alkyl terminally substituted with —C≡CH;
  d) —S—$CH_3$;
  e) cyclopropyl;
  f) —NH—($C_{1-3}$-alkyl) and —N($CH_3$)($C_{1-3}$-alkyl), wherein each alkyl group is optionally substituted with 1-3 F or one —$OCH_3$;
  g) azetidinyl, tetrahydropyranyl and morpholinyl, each optionally substituted with —$OCH_3$;
  h) tetrahydrofuranyloxy;
  i) —O—$CH_2$—$R^3$,
    wherein $R^3$ is $C_{3-4}$-cycloalkyl optionally substiuted with 1 or 2 substituents independently selected from the group consisting of F and CN;
    tetrahydropyranyl;
    piperidinyl optionally substituted with —C(=O)—$CH_3$ or —C(=O)-cyclopropyl;
    isoxazolyl, thiazolyl or thiadiazolyl;
  j) —O—CH($CH_3$)-oxazolyl;
  k) —N($R^N$)—$R^4$,
    wherein $R^N$ is H or $CH_3$, and
    $R^4$ is tetrahydrofuranyl, tetrahydropyranyl or —($CH_2$)-isoxazolyl.

$R^1$-G7:

In another embodiment the group $R^1$ is selected from the group $R^1$-G7 consisting of:

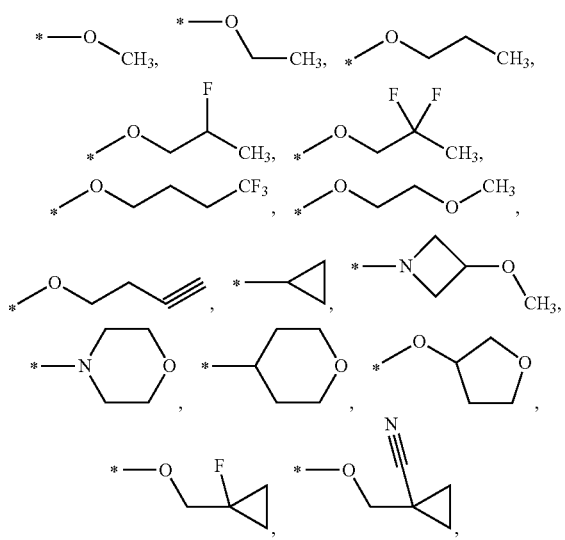

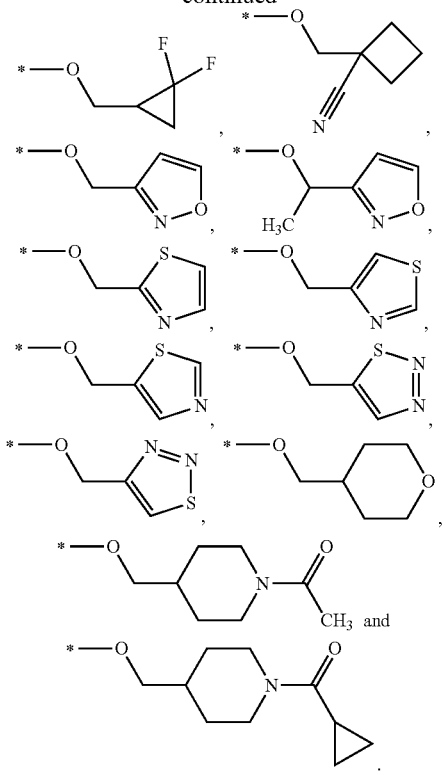

$R^2$:

$R^2$-G1:

The group $R^2$ is preferably selected from the group $R^2$-G1 as defined above.

$R^2$-G2:

In one embodiment the group $R^2$ is selected from the group $R^2$-G2 consisting of $C_{1-4}$-alkyl, $C_{3-5}$-cycloalkyl, heterocyclyl, —($C_{1-2}$-alkyl)-($C_{3-5}$-cycloalkyl), —($C_{1-2}$-alkyl)-heterocyclyl, —($C_{1-2}$-alkyl)-aryl, —($C_{1-2}$-alkyl)-heteroaryl and —($C_{1-2}$-alkyl)-C≡CH;
  wherein each heterocyclyl is a 4- to 6-membered saturated carbocyclic group, in which 1 or 2 $CH_2$-moieties are replaced by a heteroatom selected from NH, O or S; and
  wherein each aryl is selected from the group consisting of phenyl and naphthyl; and
  wherein each heteroaryl is a 5- or 6-membered heteroaromatic ring which contains 1, 2 or 3 heteroatoms independently selected from =N—, —NH—, —O— and —S—; and
  wherein each alkyl, cycloalkyl, heterocyclyl, aryl or heteroaryl group is optionally independently substituted with one or more F, Cl, CN, OH, $C_{1-2}$-alkyl, —O—($C_{1-2}$-alkyl), —C(=O)—($C_{1-2}$-alkyl) and —C(=O)—($C_{3-7}$-cycloalkyl).

$R^2$-G3:

In another embodiment the group $R^2$ is selected from the group $R^2$-G3 consisting of $C_{1-4}$-alkyl, $C_{3-4}$-cycloalkyl, heterocyclyl, —($C_{1-2}$-alkyl)-($C_{3-4}$-cycloalkyl), —($C_{1-2}$-alkyl)-heterocyclyl, —($C_{1-2}$-alkyl)-phenyl, —($C_{1-2}$-alkyl)-heteroaryl and —($C_{1-2}$-alkyl)-C≡CH;
  wherein each heterocyclyl is selected from the group consisting of azetidinyl, tetrahydrofuranyl, tetrahydrofuranyl and piperidinyl; and wherein each heteroaryl is selected from the group consisting of isoxazolyl, thiazolyl and thiadiazolyl; and wherein each alkyl, cycloalkyl, heterocyclyl, aryl or heteroaryl group is optionally independently substituted with one or more F, CN, OH, $CH_3$, $-OCH_3$, $-C(=O)-CH_3$ and $-C(=O)$-cyclopropyl.

$R^2$-G4:

In another embodiment the group $R^2$ is selected from the group $R^2$-G4 consisting of $C_{1-4}$-alkyl, $-CH_2-(C_{3-4}$-cycloalkyl), $-CH_2$-heterocyclyl, $-CH_2$-heteroaryl and $-CH_2-CH_2-C\equiv CH$;

wherein each heterocyclyl is selected from the group consisting of tetrahydro-furanyl and piperidinyl; and wherein each heteroaryl is selected from the group consisting of isoxazolyl, thiazolyl and thiadiazolyl; and wherein each alkyl, cycloalkyl, heterocyclyl, aryl or heteroaryl group is optionally independently substituted with one or more F, CN, $CH_3$, $-OCH_3$, $-C(=O)-CH_3$ and $-C(=O)$-cyclopropyl.

$R^2$-G5:

In another embodiment the group $R^2$ is selected from the group $R^2$-G5 consisting of $C_{1-4}$-alkyl, $-CH_2-(C_{3-4}$-cycloalkyl), $-CH_2$-heteroaryl and $-CH_2-CH_2-C\equiv CH$;

wherein each heteroaryl is selected from the group consisting of isoxazolyl, thiazolyl and thiadiazolyl; and wherein each alkyl, cycloalkyl, aryl or heteroaryl group is optionally independently substituted with one or more F, CN and $-OCH_3$.

Examples of preferred subgeneric embodiments according to the present invention are set forth in the following table, wherein each substituent group of each embodiment is defined according to the definitions set forth above:

| No. | A | $R^1$ | $R^2$ |
|---|---|---|---|
| 1 | A-G1 | $R^1$-G1 | $R^2$-G1 |
| 2 | A-G2 | $R^1$-G1 | $R^2$-G1 |
| 3 | A-G1 | $R^1$-G1 | $R^2$-G2 |
| 4 | A-G2 | $R^1$-G1 | $R^2$-G2 |
| 5 | A-G1 | $R^1$-G1 | $R^2$-G3 |
| 6 | A-G2 | $R^1$-G1 | $R^2$-G3 |
| 7 | A-G1 | $R^1$-G1 | $R^2$-G4 |
| 8 | A-G2 | $R^1$-G1 | $R^2$-G4 |
| 9 | A-G1 | $R^1$-G1 | $R^2$-G5 |
| 10 | A-G2 | $R^1$-G1 | $R^2$-G5 |
| 11 | A-G1 | $R^1$-G2 | $R^2$-G1 |
| 12 | A-G2 | $R^1$-G2 | $R^2$-G1 |
| 13 | A-G1 | $R^1$-G2 | $R^2$-G2 |
| 14 | A-G2 | $R^1$-G2 | $R^1$-G2 |
| 15 | A-G1 | $R^1$-G2 | $R^2$-G3 |
| 16 | A-G2 | $R^1$-G2 | $R^2$-G3 |
| 17 | A-G1 | $R^1$-G2 | $R^2$-G4 |
| 18 | A-G2 | $R^1$-G2 | $R^2$-G4 |
| 19 | A-G1 | $R^1$-G2 | $R^2$-G5 |
| 20 | A-G2 | $R^1$-G2 | $R^2$-G5 |
| 21 | A-G1 | $R^1$-G3 | $R^2$-G1 |
| 22 | A-G2 | $R^1$-G3 | $R^2$-G1 |
| 23 | A-G1 | $R^1$-G3 | $R^2$-G2 |
| 24 | A-G2 | $R^1$-G3 | $R^2$-G2 |
| 25 | A-G1 | $R^1$-G3 | $R^2$-G3 |
| 26 | A-G2 | $R^1$-G3 | $R^2$-G3 |
| 27 | A-G1 | $R^1$-G3 | $R^2$-G4 |
| 28 | A-G2 | $R^1$-G3 | $R^2$-G4 |
| 29 | A-G1 | $R^1$-G3 | $R^2$-G5 |
| 30 | A-G2 | $R^1$-G3 | $R^2$-G5 |
| 31 | A-G1 | $R^1$-G4 | $R^2$-G1 |
| 32 | A-G2 | $R^1$-G4 | $R^2$-G1 |
| 33 | A-G1 | $R^1$-G4 | $R^2$-G2 |
| 34 | A-G2 | $R^1$-G4 | $R^2$-G2 |
| 35 | A-G1 | $R^1$-G4 | $R^2$-G3 |
| 36 | A-G2 | $R^1$-G4 | $R^2$-G3 |
| 37 | A-G1 | $R^1$-G4 | $R^2$-G4 |
| 38 | A-G2 | $R^1$-G4 | $R^2$-G4 |
| 39 | A-G1 | $R^1$-G4 | $R^2$-G5 |
| 40 | A-G2 | $R^1$-G4 | $R^2$-G5 |
| 41 | A-G1 | $R^1$-G5 | $R^2$-G1 |
| 42 | A-G2 | $R^1$-G5 | $R^2$-G1 |
| 43 | A-G1 | $R^1$-G5 | $R^2$-G2 |
| 44 | A-G2 | $R^1$-G5 | $R^2$-G2 |
| 45 | A-G1 | $R^1$-G5 | $R^2$-G3 |
| 46 | A-G2 | $R^1$-G5 | $R^2$-G3 |
| 47 | A-G1 | $R^1$-G5 | $R^2$-G4 |
| 48 | A-G2 | $R^1$-G5 | $R^2$-G4 |
| 49 | A-G1 | $R^1$-G5 | $R^2$-G5 |
| 50 | A-G2 | $R^1$-G5 | $R^2$-G5 |
| 51 | A-G1 | $R^1$-G6 | — |
| 52 | A-G2 | $R^1$-G6 | — |
| 53 | A-G1 | $R^1$-G7 | — |
| 54 | A-G2 | $R^1$-G7 | — |
| 55 | A-G3 | $R^1$-G1 | $R^2$-G1 |
| 56 | A-G3 | $R^1$-G2 | $R^2$-G2 |
| 57 | A-G3 | $R^1$-G3 | $R^2$-G2 |
| 58 | A-G3 | $R^1$-G3 | $R^2$-G3 |
| 59 | A-G3 | $R^1$-G4 | $R^2$-G3 |
| 60 | A-G3 | $R^1$-G4 | $R^2$-G4 |
| 61 | A-G3 | $R^1$-G4 | $R^2$-G5 |
| 62 | A-G3 | $R^1$-G5 | $R^2$-G4 |
| 63 | A-G3 | $R^1$-G5 | $R^2$-G5 |
| 64 | A-G3 | $R^1$-G6 | — |
| 65 | A-G3 | $R^1$-G7 | — |

The following preferred embodiments of compounds of the formula (I) are described using generic formulae (I.1) to (I.2), wherein any tautomers and stereoisomers, solvates, hydrates and salts thereof, in particular the pharmaceutically acceptable salts thereof, are encompassed.

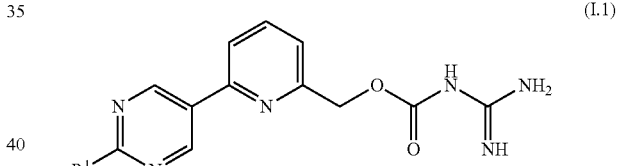

(I.1)

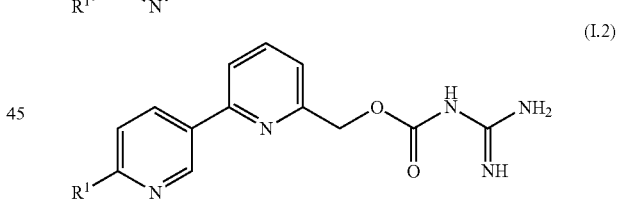

(I.2)

wherein in of the above formulae (I.1) to (I.2), the group $R^1$ is as defined above.

A preferred embodiment of the present invention concerns compounds of formula

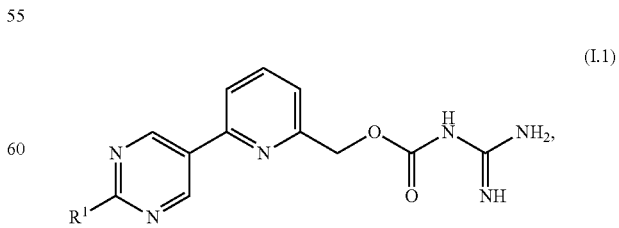

(I.1)

wherein $R^1$ is selected from the group consisting of cyclopropyl, heterocyclyl and $-O-R^2$;

wherein R² is selected from the group consisting of C₁₋₆-alkyl, —(C₁₋₂-alkyl)-(C₃₋₆-cycloalkyl), —(C₁₋₂-alkyl)-heteroaryl and —(C₁₋₂-alkyl)-C≡CH;

wherein each heterocyclyl is selected from the group consisting of azetidinyl, piperidinyl, tetrahydrofuranyl, tetrahydropyranyl and morpholinyl; and wherein each heterocyclyl group is optionally independently substituted with one substituent selected from the group consisting of F, CN, OH, CH₃, —O—CH₃; and wherein each heteroaryl is selected from the group consisting of isoxazolyl, thiazolyl and thiadiazolyl; and wherein each alkyl, cycloalkyl, heterocyclyl, or heteroaryl group is optionally independently substituted with one or more F, CN, CH₃, —OCH₃, —C(=O)—CH₃ and —C(=O)-cyclopropyl;

or a salt thereof, preferably a pharmaceutically acceptable salt thereof.

Another preferred embodiment of the present invention concerns compounds of formula (I.1), wherein R¹ is selected from the group consisting of cyclopropyl, heterocyclyl and —O—R²;

wherein R² is selected from the group consisting of C₁₋₄-alkyl, —CH₂—(C₃₋₄-cycloalkyl), —CH₂-heteroaryl and —CH₂—CH₂—C≡CH;

wherein each heteroaryl is selected from the group consisting of isoxazolyl, thiazolyl and thiadiazolyl; and wherein each alkyl, cycloalkyl, aryl or heteroaryl group is optionally independently substituted with one or more F, CN and —OCH₃.

wherein each heterocyclyl is selected from the group consisting of azetidinyl, piperidinyl, tetrahydrofuranyl, tetrahydropyranyl and morpholinyl; and wherein each heterocyclyl group is optionally independently substituted with one substituent selected from the group consisting of F, CN, OH, CH₃, —O—CH₃;

or a salt thereof, preferably a pharmaceutically acceptable salt thereof.

Preferred compounds of the invention include:

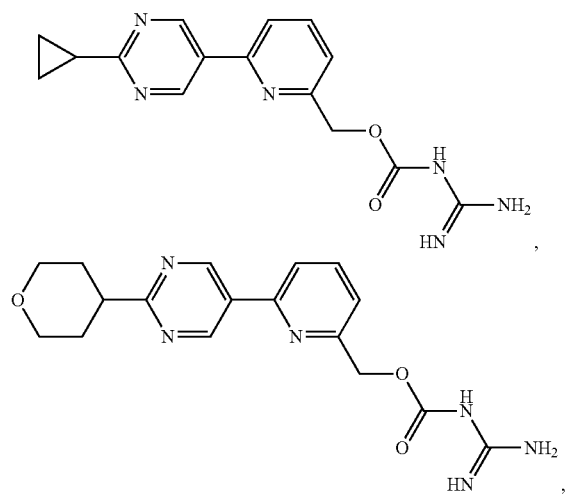

and the salts thereof, preferably the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably, the compounds are obtained analogously to the methods of preparation explained more fully hereinafter, in particular as described in the experimental section.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of AOC3 with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

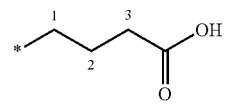

wherein the carboxy group is attached to the third carbon atom of the propyl group. The terms "1-methylpropyl-", "2,2-dimethylpropyl-" or "cyclopropylmethyl-" group represent the following groups:

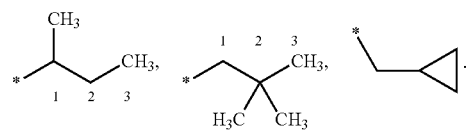

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

All rests and substituents as defined hereinbefore and hereinafter may be substituted with one or more F atoms.

Pharmacological Activity

The activity of the compounds of the invention may be demonstrated using the following AOC3 assay:

AOC3 Biochemical Assay

The MAO-Glo™ Assay (commercial available from PROMEGA, #V1402) provides a sensitive method for the measurement of monoamine oxidase (MAO) activity (Valley, M. P. et al., 2006, Anal. Biochem. 359: 238-246) from a variety of tissues, biofluids or recombinant expressed or purified enzymes. As substrate a derivate of the beetle luciferin ((4S)-4,5-dihydro-2-(6-hydroxybenzothiazolyl)-4-thiazole-carboxylic acid) is used, which is oxidized at a primary amine moiety. After a spontaneous elimination and a catalyzed esterase reaction, the turnover of the luciferine by the luciferase is recorded as a signal of AOC3 activity.

For the determination of AOC3 activity or compound inhibition potency, the compound inhibitors are dissolved in DMSO and adjusted to the respective assay concentration with reaction buffer (50 mM HEPES, 5 mM KCl, 2 mM $CaCl_2$, 1.4 mM $MgCl_2$, 120 mM NaCl, 0.001% (v/v) Tween 20, 100 µM TCEP, pH 7.4). An aliquot of 3 µL of the compound dilution is added to a 384 well plate (Optiplate, PS, flat bottom, white, PERKIN ELMER, #6007290) with a final DMSO concentration of 6.6%. Recombinant CHO cells, overexpressing the human (1500 cells/well), mouse (1000 cells/well) or rat (500 cells/well) AOC3 enzyme are diluted in reaction buffer and added in a volume of 15 µL to the wells. After incubation for 20 minutes at 37° C., 2 µL of MAO substrate (dissolved in DMSO at 16 mM, adjusted to assay concentration in reaction buffer to a final assay concentration of 20 µM) is added and further incubated for 60 minutes at 37° C. The turnover of the substrate is determined by the addition of 20 µL of the detection-mix which was generated by the addition of reconstitution buffer with esterase (PROMEGA, #V1402) to the luciferine detection reagent (PROMEGA, #V1402). After an incubation period of 20 minutes, the luminescent signal is measured with Envision 2104 Multilabel Reader (PERKIN ELMER).

Alternative assays for the determination of the AOC3 enzymatic activity could be the extraction of $^{14}C$-labelled benzylamine reaction product or the Amplex Red Monoamine Oxidase reaction (Molecular Probes, Netherlands) as described in Gella et al. (Gella, A. et al., 2013, J. Neural Transm. 120: 1015-1018).

The compounds of general formula (I) according to the invention for example have $IC_{50}$ values below 5000 nM, particularly below 1000 nM, preferably below 300 nM, most preferably below 100 nM.

AOC1 Biochemical Assay

The Amplex® Red Assay (available from Thermo Fisher Scientific) provides a sensitive method for the detection of $H_2O_2$ generated during enzymatic reactions like the amine oxidation catalyzed by AOC1. The assay reagent is a colorless substrate (N-acetyl-3,7-dihydroxyphenoxazine) that reacts in a 1:1 stoichiometry with hydrogen peroxide ($H_2O_2$) to produce the fluorescent dye resorufin (7-hydroxyphenoxazin-3-one, excitation/emission maxima=570/585 nm).

For the determination of AOC1 activity or compound AOC1 inhibition potency, the compound inhibitors are dissolved in DMSO and adjusted to the respective assay concentration with reaction buffer (100 mM sodiumphosphate, 0.05% Pluronic F-127 (#P3000MP Sigma-Aldrich), pH 7.4). An aliquot of 3 µL of the compound dilution is added to a 384 well plate (Optiplate, PS, flat bottom F, black, PERKIN ELMER, #6007270) in a DMSO concentration of 6.6%.

An AOC1 enzyme aliquot (#8297-AO-010, R&D Systems) is thawed on ice, diluted in reaction buffer and added in a volume of 7 µL to the wells to give a final assay concentration of 1 ng/well. After incubation of inhibitor and enzyme for 30 minutes at 37° C., the enzymatic reaction is started with the addition of 10 µL of Amplex® Red reaction mix (final assay concentration: 100 mM sodiumphosphate, 120 µM Amplex® Red reagent (#A22177 Molecular Probes), 1.5 U/mL Horseradish Peroxidase (#P8375 Sigma-Aldrich), 200 µM putrescine (#P7505 Sigma-Alrdich), 0.05% Pluronic F-127 (#P3000MP Sigma-Aldrich), pH 7.4, 37° C.).

After an incubation for 30 minutes at 37° C. the turnover of the substrate is determined directly (or after the addition of an excess of an amine-oxidase inhibitor) with a fluorescence reader (Ex 540 nm/Em 590 nm) like Envision 2104 Multilabel Reader (PERKIN ELMER).

In the following table the activity expressed as $IC_{50}$ (nM) of compounds according to the invention is presented wherein the $IC_{50}$ values are determined in the AOC3 and AOC1 assay as described hereinbefore. The term "Example" refers to the example numbers according to the following experimental section.

TABLE 1

Biological data of the compounds of the present invention as obtained in the AOC3 and AOC1 assays.

| Example | AOC3 $IC_{50}$ | AOC1 $IC_{50}$ |
| --- | --- | --- |
| 01 | 27 nM | 7604 nM |
| 02 | 10 nM | 8074 nM |
| 03 | 8 nM | 8034 nM |
| 04 | 5 nM | 1723 nM |

TABLE 1-continued

Biological data of the compounds of the present invention as obtained in the AOC3 and AOC1 assays.

| Example | AOC3 IC$_{50}$ | AOC1 IC$_{50}$ |
|---|---|---|
| 05 | 15 nM | 2392 nM |
| 06 | 15 nM | 10163 nM |
| 07 | 5 nM | 2011 nM |
| 08 | 4 nM | 2689 nM |
| 09 | 7 nM | 1415 nM |
| 10 | 11 nM | 3478 nM |
| 11 | 5 nM | 2394 nM |
| 12 | 5 nM | 7530 nM |
| 13 | 2 nM | 1479 nM |
| 14 | 3 nM | 1336 nM |
| 15 | 8 nM | 5194 nM |
| 16 | 9 nM | 718 nM |
| 17 | 5 nM | 3616 nM |
| 18 | 3 nM | 1401 nM |
| 19 | 9 nM | n.D. |
| 20 | 5 nM | 7207 nM |
| 21 | 4 nM | 3192 nM |
| 22 | 3 nM | 2374 nM |
| 23 | 2 nM | 3817 nM |
| 24 | 4 nM | 1585 nM |
| 25 | 3 nM | 483 nM |
| 26 | 3 nM | 2520 nM |
| 27 | 4 nM | 3770 nM |
| 28 | 15 nM | 3288 nM |
| 29 | 2 nM | 659 nM |
| 30 | 3 nM | 978 nM |
| 31 | 3 nM | 612 nM |
| 32 | 2 nM | 710 nM |
| 33 | 3 nM | 899 nM |
| 34 | 2 nM | 503 nM |
| 35 | 3 nM | 1022 nM |
| 36 | 5 nM | 1153 nM |
| 37 | 3 nM | 227 nM |
| 38 | 3 nM | 322 nM |

AOC1 expression and enzymatic activity is mainly found in the gut, placenta and kidney. The enzyme catalyzes the oxidation of primary amines derived from nutrition and protects the individuum from cardiometabolic effects of histamine, putrescine, tryptamine and cadaverine. Inhibition of AOC1 can lead to impaired tolerance to ingested histamine, resulting in increased plasma and tissue histamine-levels which can cause adverse events or undesirable side effects like decreased aterial pressure and compensation by increased heart-rate, tachycardia, headache, flush, urticaria, pruritus, bronchospasm and cardiac arrest (Maintz L. and Novak N. 2007. Am. J. Clin. Nutr. 85:1185-96). The consequence of AOC1 inhibition in combination with histamine intake has been demonstrated in experiments with pigs: After the injection of the AOC1 inhibitor aminoguanidine (100 mg/kg) and gavage of histamine (2 mg/kg) animals experienced increased histamine blood levels accompanied with a drop of blood pressure, increased heart rate, flushing, vomiting and death (3 out of 15 animals) (Sattler J. 1988. Agents and Actions, 23: 361-365) under the experimental conditions. Histamine intolerance in humans was associated to mutations in the promoter region of AOC1, leading to reduced mRNA expression and plasma AOC1 activity (Maintz et al. 2011. Allergy 66: 893-902).

Therefore, it was an aim of the invention to provide compounds with a low activity on AOC1, in order to avoid such undesired side-effects.

Thus, the AOC1 activity was measured, and, suprisingly, it was found out that the pyridinyl compounds of the present invention exhibit an high selectivity towards AOC1.

It has now been found out that, surprisingly, the compounds according to the present invention are more selective towards AOC1 than the corresponding prior art compounds as described in EP 2 695 881, i.e. the replacement of the fluoro-substituted phenyl moiety (adjacent to the guanidine function) by a pyridinyl moiety results in compounds with a highly increased selectivity towards AOC1, without affecting the activity towards AOC3. The selectivity towards AOC1 was tested according to the AOC1 assay as described above.

TABLE 2

Biological data of certain compounds of EP 2 695 881 (corresponding to WO 2012/124696) as obtained in the AOC3 and AOC1 assays as described above and comparison with the corresponding compounds of the invention.

| Structure | IC$_{50}$ AOC3 | IC$_{50}$ AOC1 | Comparison compound of present invention |
|---|---|---|---|
| Ex. 136, p. 235 | 6 nM | 60 nM | Ex. 5:<br>IC$_{50}$ AOC3: 15 nM<br>IC$_{50}$ AOC1: 2392 nM |
| Ex. 197, p. 243 | 6 nM | 97 nM | Ex. 10:<br>IC$_{50}$ AOC3: 11 nM<br>IC$_{50}$ AOC1: 3478 nM |

TABLE 2-continued

Biological data of certain compounds of EP 2 695 881 (corresponding to
WO 2012/124696) as obtained in the AOC3 and AOC1 assays as described
above and comparison with the corresponding compounds of the invention.

| Structure | IC$_{50}$ AOC3 | IC$_{50}$ AOC1 | Comparison compound of present invention |
|---|---|---|---|
| Ex. 63, p. 227 | 1 nM | 100 nM | Ex. 13:<br>IC$_{50}$ AOC3: 2 nM<br>IC$_{50}$ AOC1: 1479 nM |
| Ex. 81, p. 229 | 1 nM | 174 nM | Ex. 14:<br>IC$_{50}$ AOC3: 3 nM<br>IC$_{50}$ AOC1: 1336 nM |
| Ex. 11, p. 221 | 1 nM | 6 nM | Ex. 37:<br>IC$_{50}$ AOC3: 3 nM<br>IC$_{50}$ AOC1: 227 nM |
| Ex. 74, p. 229 | 1 nM | 8 nM | Ex. 38:<br>IC$_{50}$ AOC3: 3 nM<br>IC$_{50}$ AOC1: 322 nM |

In view of their ability to inhibit AOC3, the compounds of general formula (I) according to the invention and the corresponding salts thereof are suitable for the treatment, including preventative treatment of all those diseases or conditions which may be affected or which are mediated by the inhibition of AOC3 activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of AOC3 in a patient, preferably in a human.

In yet another aspect the present invention relates a method for treating, including preventing a disease or condition mediated by the inhibition of AOC3 in a mammal that includes the step of administering to a patient, preferably a human, in need of such treatment a therapeutically effective amount of a compound of the present invention, or a pharmaceutical composition thereof.

Diseases and conditions mediated by inhibitors of AOC3 embrace NASH (non-alcoholic steatohepatitis), pulmonary fibrosis, retinopathy or nephropathy.

According to one aspect the compounds of the present invention are particularly suitable for treating inflammatory diseases, such as vascular inflammatory diseases, arthritis, acute and chronic joint inflammation; eczema, such as atopic eczema, psoriasis ulcerative and rheumatoid psoriasis; pain, particularly musculoskeletal or nociceptive pain; inflammatory bowel disease, particularly non-infectious inflammatory bowel disease; multiple sclerosis; scleroderma, pulmonary diseases such as respiratory distress syndrome, asthma, pulmonary fibrosis, iodiopathic pulmonary fibrosis (IPF), chronic obstructive pulmonary disease (COPD) and idiopathic inflammatory disease; nephropathy, diabetic proteinuria, kidney fibrosis; diabetic retinopathy or diabetic oedema such as macular diabetic oedema; cancer, particularly melanoma and lymphoma; hepatocellular carcinoma, unspecified Colitis, rheumatoid Crohn's disease Colitis; biliary tract diseases, primary biliary cholangitis, primary sclerosing cholangitis, non-alcoholic steatohepatitis (NASH), non-alcoholic fatty liver disease (NAFLD), alcoholic liver disease, liver fibrosis, liver cirrhosis; ulcerative reperfusion injury, cerebral ischaemia and transplant rejection.

According to another aspect the compounds of the present invention are particularly suitable for treating inflammatory diseases, such as vascular inflammatory diseases, arthritis and inflammatory bowel disease, particularly non-infectious inflammatory bowel disease; pulmonary fibrosis and iodiopathic pulmonary fibrosis; diabetic retinopathy or diabetic oedema such as macular diabetic oedema; unspecified Colitis, rheumatoid Crohn's disease Colitis; biliary tract diseases, primary biliary cholangitis, primary sclerosing cholangitis, non-alcoholic steatohepatitis (NASH), non-alcoholic fatty liver disease (NAFLD), alcoholic liver disease, liver fibrosis, and liver cirrhosis.

The dose range of the compounds of general formula (I) applicable per day is usually from 0.001 to 10 mg per kg body weight of the patient, preferably from 0.01 to 8 mg per kg body weight of the patient. Each dosage unit may conveniently contain 0.1 to 1000 mg of the active substance, preferably it contains between 0.5 to 500 mg of the active substance.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon the patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with the metabolic syndrom, diabetes, obesity, cardiovascular diseases, NASH (non-alcoholic steatohepatitis), pulmonary fibrosis, retinopathy and/or nephropathy.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, anti-fibrotic agents, agents for the treatment of malignant tumors, antithrombotic agents, anti-angiogenesis agents, agents for the treatment of heart failure and agents for the treatment of complications caused by diabetes or associated with diabetes.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of AOC3, in particular diseases or conditions as described hereinbefore and hereinafter.

In yet another aspect the present invention relates a method for treating, including preventing a disease or condition mediated by the inhibition of AOC3 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Synthesis Schemes

Typical methods of preparing the compounds of the invention are described in the experimental section.

The potent inhibitory effect of the compounds of the invention can be determined by in vitro enzyme assays as described in the experimental section.

The compounds of the present invention may also be made by methods known in the art including those described below and including variations within the skill of the art.

Scheme 1:

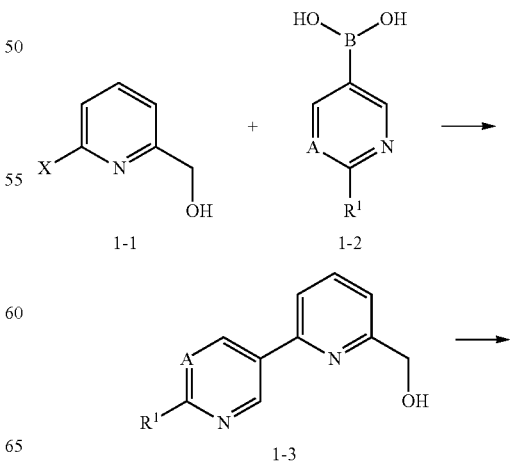

23

-continued

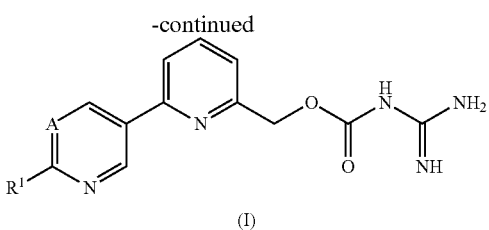

(I)

Compounds of the general formula I, wherein A and $R^1$ are as previously defined, can be prepared via the process outlined in scheme 1 using a compound of the general formula 1-1, wherein X is a halogen, with an boronic acid or corresponding pinacolate 1-2, in presence of a palladium catalyst and ligand and a base in appropriate solvents such as dioxane at a temperature between 0° C. and 150° C. (Suzuki-coupling, *Chem. Rev.*, 1995, 95 (7), 2457). The reaction of the benzylic alcohol of the general formula 1-3, wherein A and $R^1$ are as previously defined, in order to obtain a compound of the general formula I, wherein A and $R^1$ are as previously defined, may be achieved via the acylation with CDI followed by reaction with a guanidine salt in an appropriate solvent such as DMF. If reasonable, the reaction sequence to obtain compounds of the general formula I can also be reversed.

Scheme 2:

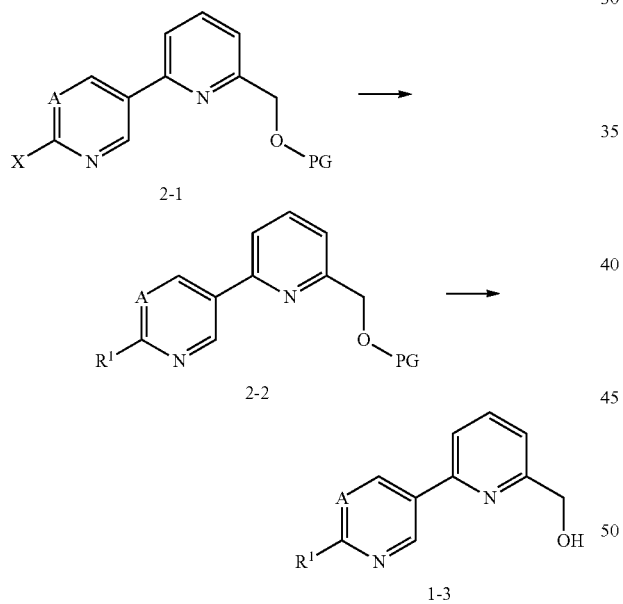

Intermediates of the general formula 1-3, wherein A and $R^1$ are as previously defined, can be prepared via the process outlined in scheme 2 using a compound of the general formula 2-1, wherein A is as previously defined and X is a suitable leaving group, such as halogen or S(=O)Me, and PG is a suitable protecting group, such as $Si^tBuMe_2$, and a nucleophile in presence of a base such as NaH, DIPEA or DBU in appropriate solvents such as THF and DCM at a temperature between 0° C. and 150° C. To obtain the benzyl alcohol intermediate 1-3 wherein A and $R^1$ are as previously defined, the protecting group has to be removed using suitable conditions, for example TBAF or TFA in THF for the $Si^tBuMe_2$ group. In certain cases, the acylguanidine

24 moiety can also be employed as protecting group and compounds of the general formula I can be directly obtained in one step from the corresponding intermediate 2-1.

Scheme 3:

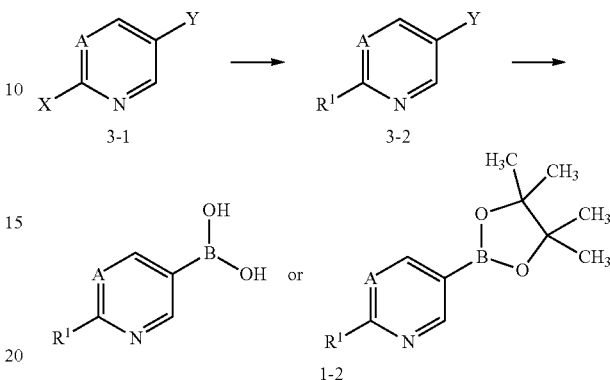

Intermediates of the general formula 1-2, wherein A and $R^1$ are as previously defined, can be prepared via the processes outlined in scheme 3 using a compound of the general formula 3-1, wherein A is as previously defined and X and Y are a halogen and $R^1$—H is a nucleophile in presence of a base such as DIPEA in appropriate solvents such as acetonitrile at a temperature between 0° C. and 150° C. Alternatively, zinc-reagents and Negishi-coupling conditions (*Handbook of Organopalladium Chemistry for Organic Synthesis*, (ed. Negishi, E.-I.), 1, 229-247, (John Wiley & Sons Inc., New York, 2002) can be used. To obtain the boronic acid or corresponding pinacol ester intermediate 1-2 wherein A and $R^1$ are as previously defined a Suzuki-Miyaura Borylation (*J. Am. Chem. Soc.*, 2002, 124, 8001) or a halogen-metal exchange followed by reaction with a suitable electrophile, using reagent such as n-BuLi and $B(O^iPr)_3$, can be used.

Scheme 4:

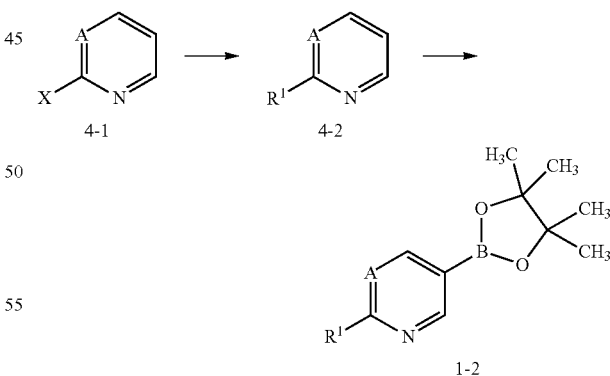

Alternatively, the reaction of a compound of the general formula 4-1, wherein A is as previously defined and X is halogen and $R^1$—H is a nucleophile in presence of a base such as $K_2CO_3$ in appropriate solvents such as acetonitrile at a temperature between 0° C. and 150° C. furnishes the intermediate 4-2, wherein A and $R^1$ are as previously defined. To obtain the boronic acid pinacol ester intermediate 1-2 wherein A and $R^1$ are as previously defined, the Ir-catalyzed reaction as described by Hartwig et al (*J. Am. Chem. Soc.*, 2014, 136 (11), 4287) can be utilized (scheme 4).

Scheme 5:

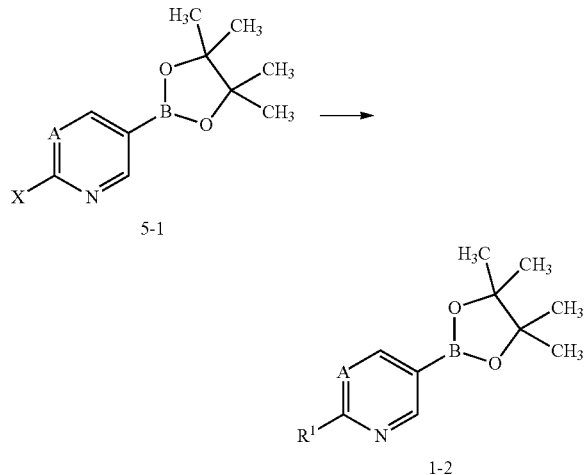

Alternatively, the reaction of a compound of the general formula 5-1, wherein A is as previously described and X is halogen and R¹—H is a nucleophile in presence of a base such as NEt₃ in appropriate solvents such as dioxane at a temperature between 0° C. and 150° C. can be used to obtain intermediate 1-2, wherein A and R¹ are as previously defined (scheme 5).

The synthetic routes presented may rely on the use of protecting groups. For example, reactive groups present, such as hydroxy, carbonyl, carboxy, amino, alkylamino or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

Experimental Part

The Examples that follow are intended to illustrate the present invention without restricting it. The terms "ambient temperature" and "room temperature" are used interchangeably and designate a temperature of about 20° C.

The hereinafter described compounds have been characterized through their characteristic mass after ionisation in a mass-spectrometer and their retention time on an analytical HPLC.

LIST OF ABBREVIATIONS

ACN Acetonitrile
aq. Aqueous
° C. Degree celsius
CDI Di(imidazol-1-yl)methanone
DA Diode array
DCM Dichloromethane
DBU 1,8-Diazabicyclo[5.4.0]undec-7-ene
DIPEA N-ethyl-N-isopropyl-propan-2-amine
DMF N,N-dimethylformamide
eq Equivalent
ESI-MS Electrospray ionisation mass spectrometry
EtOAc/EE Ethyl acetate
FC Flash-cromatography, SiO₂ is used if no further details given
GP General procedure
h Hour
HPLC High performance liquid chromatography
KOAc Potassium acetate
K₂OC₃ Potassium carbonate
L Liter
MeOH Methanol
min Minute
ml Milliliter
mp Melting point
MS Mass spectrum
NaH Sodium hydride
NaHCO₃ Sodium bicarbonate
n.d. Not determined
Pd(PPh₃)₄ Tetrakis(triphenylphosphine)palladium(0)
Pd(dppf)Cl₂ [1,1'-Bis(diphenylphosphino)ferrocene]dichloropalladium(II)
RT Room temperature (about 20° C.)
R_t Retention time
TBAF Tetrabutylammonium fluoride
TF/TFA Trifluoroacetic acid
THF Tetrahydrofuran
TLC Thin-layer chromatography on SiO₂
XPhos Pd G2 Chloro(2-dicyclohexylphosphino-2',4',6'-triisopropyl-1,1'-biphenyl)[2-(2'-amino-1,1'-biphenyl)]palladium(II)

HPLC-A: Agilent 1200 with DA- and MS-Detector, Sunfire C18_3.0×30 mm, 2.5 μm (Waters), 60° C.

| Time [min] | % Sol [H₂O 0.1% TFA] | % Sol [ACN] | Flow [mL/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

HPLC-B: Waters Acquity with DA- and MS-Detector, Sunfire C18_2.1×30 mm, 2.5 μm (Waters), 60° C.

| Time [min] | % Sol [H₂O 0.1% TFA] | % Sol [ACN] | Flow [ml/min] |
|---|---|---|---|
| 0.0 | 99.0 | 1.0 | 1.5 |
| 0.02 | 99.0 | 1.0 | 1.5 |
| 1.0 | 0.0 | 100.0 | 1.5 |
| 1.1 | 0.0 | 100.0 | 1.5 |

HPLC-C: Agilent 1200 with DA- and MS-detector, XBridge C18_3.0×30 mm, 2.5 μm (Waters), 60° C.

| Time [min] | % Sol [H₂O 0.1% NH₄OH] | % Sol [ACN] | Flow [ml/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

HPLC-D: Waters Acquity with DA- and MS-Detector, XBridge BEH C18_2.1×30 mm, 1.7 μm (Waters), 60° C.

| Time [min] | % Sol [H₂O 0.1% TFA] | % Sol [ACN] | Flow [ml/min] |
|---|---|---|---|
| 0.0 | 99.0 | 1.0 | 1.6 |
| 0.02 | 99.0 | 1.0 | 1.6 |
| 1.0 | 0.0 | 100.0 | 1.6 |
| 1.1 | 0.0 | 100.0 | 1.6 |

HPLC-E: Agilent 1100 with DA- and MS-detector, Sunfire C18_3.0×30 mm, 2.5 μm (Waters), 60° C.

| Time [min] | % Sol [H₂O 0.1% TFA] | % Sol [ACN] | Flow [ml/min] |
|---|---|---|---|
| 0.0 | 98.0 | 2.0 | 2.0 |
| 1.2 | 0.0 | 100.0 | 2.0 |
| 1.4 | 0.0 | 100.0 | 2.0 |

HPLC-F: Waters Acquity with QDa-Detector, Sunfire C18_3.0×30 mm, 2.5 μm (Waters), 60° C.

| Time [min] | % Sol [H₂O 0.1% TFA] | % Sol [ACN] | Flow [ml/min] |
|---|---|---|---|
| 0.0 | 95.0 | 5.0 | 1.5 |
| 1.3 | 0.0 | 100.0 | 1.5 |
| 1.5 | 0.0 | 100.0 | 1.5 |
| 1.6 | 95.0 | 5.0 | 1.5 |

HPLC-G: Waters Acquity with QDa-Detector, Sunfire C18_3.0×30 mm, 2.5 μm (Waters), 60° C.

| Time [min] | % Sol [H₂O 0.1% NH₄OH] | % Sol [ACN] | Flow [ml/min] |
|---|---|---|---|
| 0.0 | 95.0 | 5.0 | 1.5 |
| 1.3 | 0.0 | 100.0 | 1.5 |
| 1.5 | 0.0 | 100.0 | 1.5 |
| 1.6 | 95.0 | 5.0 | 1.5 |

HPLC-H: Waters Acquity with QDa-Detector, Sunfire C18_3.0×30 mm, 2.5 μm (Waters), 40° C.

| Time [min] | % Sol [H₂O 0.1% TFA] | % Sol [ACN 0.08% TFA] | Flow [ml/min] |
|---|---|---|---|
| 0.0 | 95.0 | 5.0 | 1.5 |
| 1.3 | 0.0 | 100.0 | 1.5 |
| 1.5 | 0.0 | 100.0 | 1.5 |
| 1.6 | 95.0 | 5.0 | 1.5 |

I.1 5-[6-(tert-Butyl-dimethyl-silanyloxymethyl)-pyridin-2-yl]-2-methanesulfinyl-pyrimidine

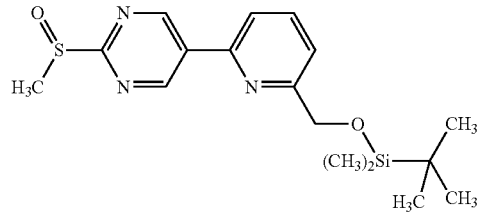

To a mixture of 10.00 g (53.19 mmol) 2-bromo-6-(hydroxymethyl)pyridine, 8.69 g (127.65 mmol) imidazole and DMF 10.42 g (69.14 mmol) tert-butyl-chloro-dimethyl-silane are added and the mixture is stirred at RT overnight. The reaction mixture is diluted with EtOAc and washed with water, dried and evaporated. The crude product is purified by FC yielding 16 g 2-bromo-6-(tert-butyl-dimethyl-silanyloxymethyl)-pyridine To a mixture of 1.04 g (3.24 mmol) 2-bromo-6-(tert-butyl-dimethyl-silanyloxymethyl)-pyridine, 662 mg (3.89 mmol) (2-methylsulfanylpyrimidin-5-yl)boronic acid, 4.3 ml (8.6 mmol) 2 M Na₂CO₃ sol. in H₂O and dioxane, 265 mg (0.325 mmol) Pd(dppf)Cl₂*DCM is added and the reaction mixture is stirred at 90° C. overnight. The reaction mixture is diluted with water and extracted with EtOAc. The organic phases are pooled and washed with water and brine, dried with MgSO₄ and evaporated. The crude product is purified by FC yielding 1.05 g tert-butyl-dimethyl-[[6-(2-methylsulfanylpyrimidin-5-yl)-2-pyridyl]methoxy]silane.

A mixture of 2.00 g (5.76 mmol) tert-butyl-dimethyl-[[6-(2-methylsulfanylpyrimidin-5-yl)-2-pyridyl]methoxy]silane and DCM is cooled in an ice bath and 1.32 g (5.76 mmol) 75% 3-chlorobenzenecarboperoxoic acid are slowly added and the mixture is stirred at 0° C. for 1 h and at RT for 2 h. The reaction mixture is diluted with DCM and washed with saturated NaHCO₃ solution and water, dried with Na₂SO₄ and evaporated.

Yield: 2.03 g (97%), ESI-MS: m/z=364 (M+H)⁺, R$_t$(HPLC): 1.19 min (HPLC-A)

I.2 tert-butyl-[[6-(2-chloropyrimidin-5-yl)-2-pyridyl]methoxy]-dimethyl-silane

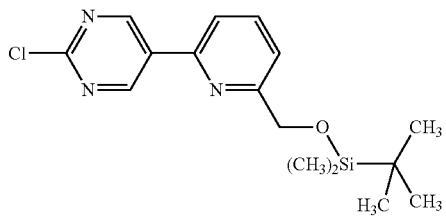

A mixture of 0.6 g (2 mmol) (6-bromo-2-pyridyl)methoxy-tert-butyl-dimethyl-silane (vide supra) and THF is cooled to −70° C. and 0.9 ml 2.3 M solution of n-hexyl lithium in hexane (2.1 mmol) is added, followed by 2.0 ml 1 M solution of $ZnCl_2$ in diethyl ether (2.0 mmol). The mixture is allowed to reach RT and stirred for 30 min. Then 0.1 g (0.1 mmol) $Pd(PPh_3)_4$ and 0.2 g (1 mmol) 2-chloro-5-iodopyrimidine in THF is added. The mixture is stirred at RT overnight, diluted with sat. $NaHCO_3$-solution and extracted with EtOAc. The organic phases are pooled, dried and evaporated and the residue is purified by FC on aluminium oxide.

Yield: 0.1 g (30%), ESI-MS: m/z=336/338 (M+H)$^+$, $R_t$(HPLC): 1.33 min (HPLC-A)

I.3 [6-(6-fluoro-3-pyridyl)-2-pyridyl]methyl N-carbamimidoylcarbamate

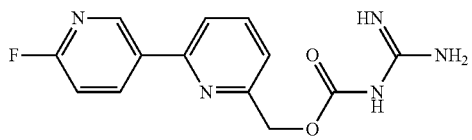 [SMILES: N=C(N)NC(=O)OCc1cccc(-c2ccc(F)nc2)n1]

A mixture 0.4 g (1.47 mmol) of intermediate III.1, 0.23 g (1.6 mmol) (6-fluoro-3-pyridyl)boronic acid, 4 ml 1M $K_3PO_4$-solution in water (4 mmol) and 0.12 g (0.14 mmol) XPhos Pd G2 in dioxane are heated to 90° C. for 2 h, then cooled to RT, diluted with water and extracted with EtOAc. The organic phases are pooled, washed with water and brine, dried and evaporated. The residue is triturated with ether and filtered.

Yield: 0.22 g (52%), ESI-MS: m/z=290 (M+H)$^+$, $R_t$(HPLC): 0.37 min (HPLC-B)

The following Intermediates can be obtained according to the given references.

| # | Structure/Reference |
|---|---|
| II.50 | 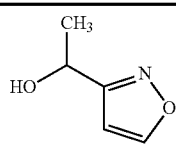<br>US2011/98272 |
| II.51 | 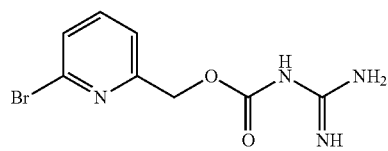 [SMILES: N=C(N)NC(=O)OCc1cccc(Br)n1]<br>WO2012/66070 |
| III.50 | 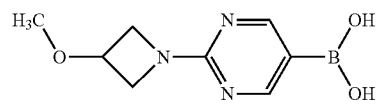<br>WO2009/120789 |

III.1 (6-bromo-2-pyridyl)methyl N-carbamimidoylcarbamate

To a mixture of 3.0 g (16.0 mmol) (6-bromo-2-pyridyl)methanol and DMF 3.9 g (24.1 mmol) CDI is added and the mixture is stirred at RT for 2 h. Then 5.8 g (32.0 mmol) guanidine carbonate are added and the reaction mixture is stirred at RT overnight, then diluted with water and cooled in an ice bath. After 1 h the precipitate is filtered off, washed with cold water and dried.

Yield: 3.7 g (85%), ESI-MS: m/z=273 (M+H)$^+$, $R_t$(HPLC): 0.70 min (HPLC-C), mp=168-172° C.

IV.1 2-(3-methoxyazetidin-1yl)-5-(4,4,5,5-tetramethyl-1,3,2-dioxaborolan-2-yl)pyrimidine A mixture of 1.4 g (10.92 mmol) 3-methoxy-azetidine hydrochloride, 2.9 g (12.10 mmol) 2-chloro-5-iodo-pyrimidine, 3.0 ml (17.61 mmol) DIPEA and ACN are heated to 50° C. overnight. The solvent is evaporated and the crude product purified by FC giving rise to 2.8 g 5-iodo-2-(3-methoxyazetidin-1-yl)pyrimidine.

A mixture of 0.5 g (1.72 mmol) 5-iodo-2-(3-methoxyazetidin-1-yl)pyrimidine, 0.6 g (2.23 mmol) bis(pinacolato)diborone, 0.5 g (5.30 mmol) KOAc, 71 mg (0.087 mmol) Pd(dppf)Cl$_2$*DCM and dioxane is heated to 100° C. overnight. After cooling to RT, the reaction mixture is filtered through a pad of Celite and evorated. The crude product is purified by FC.

Yield: 300 mg (84%), ESI-MS: m/z=210 (M+H)$^+$, $R_t$(HPLC): 0.25 min (HPLC-D)

IV.2 (2,2-Difluoro-propyl)-[5-(4,4,5,5-tetramethyl-[1,3,2]dioxaborolan-2-yl-pyrimidin-2-yl]-amine

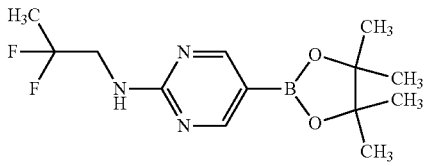

A mixture of 70 mg (0.29 mmol) 2-chloro-5-(4,4,5,5-tetramethyl-1,3,2-dioxaborolan-2-yl)pyrimidine, 42 mg (0.32 mmol) 2,2-difluoro-propylamine hydrochloride, 0.13 ml (0.93 mmol) triethylamine and dioxane is heated to 90° C. for 1 h. After cooling to RT the reaction mixture is diluted with aqueous NaCl solution. The precipitate is filtered off, washed with water and dried.

Yield: 110 mg (126%), ESI-MS: m/z=218 (M+H)$^+$, R$_t$(HPLC): 0.30 min (HPLC-B)

IV.3 N,N-dimethyl-5-(4,4,5,5-tetramethyl-1,3,2-dioxaborolan-2-yl)pyrimidin-2-amine

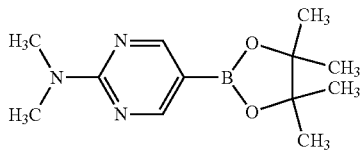

A mixture of 22.5 ml (45.5 mmol) solution of dimethylamine in THF, 3.0 g (15.5 mmol) 2-chloro-5-bromo-pyrimidine and ACN are stirred at RT for 1 h. The solvent is evaporated, water is added and the mixture is extracted with EtOAc. The organic phases are pooled, dried and evaporated yielding 3.2 g 5-bromo-N,N-dimethyl-pyrimidin-2-amine.

A mixture of 0.5 g (2.48 mmol) 5-bromo-N,N-dimethyl-pyrimidin-2-amine, 0.8 g (3.24 mmol) bis(pinacolato)diborone, 0.6 g (6.38 mmol) KOAc, 0.2 g (0.25 mmol) Pd(dppf)Cl2*DCM and dioxane is heated to 100° C. for 4.5 h. After cooling to RT, the reaction mixture is filtered through a pad of Celite and evorated, water is added and the mixture is extracted with EtOAc. The organic phases are pooled, dried and evaporated The crude product is purified by FC.

Yield: 0.6 g (96%), ESI-MS: m/z=250 (M+H)$^+$, R$_t$(HPLC): 0.22 min (HPLC-A)

IV.4 2-tetrahydropyran-4-yl-5-(4,4,5,5-tetramethyl-1,3,2-dioxaborolan-2-yl)pyrimidine

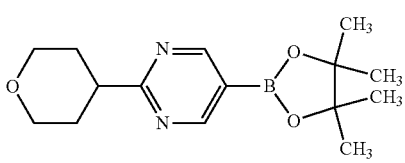

A mixture of 1.0 g (3.5 mmol) 5-bromo-2-iodo-pyrimidine, 0.2 g (0.18 mmol) Pd(PPh$_3$)$_4$ and THF is cooled to 0° C. and 14 ml (7.0 mmol) 0.5 M solution of iodo(tetrahydropyran-4-yl)zinc is added, The mixture is allowed to reach RT and stirred overnight. Then additional Pd(PPh$_3$)$_4$ and 5 ml (2.5 mmol) 0.5 M solution of iodo(tetrahydropyran-4-yl)zinc is added and the mixture stirred at RT for 4 h, diluted with sat. NaHCO$_3$-solution and EtOAc, filtered through celite and extracted with EtOAc. The organic phases are pooled, washed with water and brine, dried and evaporated and the residue is purified by FC yielding 0.41 g 5-bromo-2-tetrahydropyran-4-yl-pyrimidine.

A mixture of 0.4 g (2.48 mmol) 5-bromo-2-tetrahydropyran-4-yl-pyrimidine, 0.54 g (2.14 mmol) bis(pinacolato)diborone, 0.49 g (4.94 mmol) KOAc, 0.07 g (0.25 mmol) Pd(dppf)Cl2 and dioxane is heated to 90° C. for 1.5 h. After cooling to RT, the reaction mixture is diluted with water and extracted with EtOAc. The organic phases are pooled, washed with water and brine and dried. Charcoal is added, the mixture is filtered through Celite and evaporated.

Yield: 0.4 g (84%), ESI-MS: m/z=291 (M+H)$^+$, R$_t$(HPLC): 0.30 min (HPLC-B)

IV.5 2-propoxy-5-(4,4,5,5-tetramethyl-1,3,2-dioxaborolan-2-yl)pyrimidine

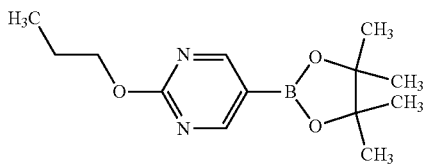

A mixture of 1.0 g (5.2 mmol) 2-chloro-5-bromo-pyrimidine, 1.4 g (10.3 mmol) K$_2$CO$_3$ and 10 ml n-propanol are stirred at RT for 48 h. The reaction mixture is diluted with water and EtOAc. The organic phase is washed with brine, dried and evaporated yielding 1.2 g 5-bromo-2-propoxy-pyrimidine.

The mixture of 0.5 g (2.00 mmol) 5-bromo-2-propoxy-pyrimidine, 0.6 g (2.20 mmol) bis(pinacolato)diborone, 0.4 g (4.00 mmol) KOAc, 0.2 g (0.20 mmol) Pd(dppf)Cl$_2$*DCM and dioxane is heated to 100° C. for 2 h. After cooling to RT, the reaction mixture is diluted with EtOAc and filtered through Celite. The filtrate is evaporated and the residue purified by FC.

Yield: 0.5 g (85%), R$_t$(HPLC): 0.74 min (HPLC-A)

IV.6 2-(2,2-difluoropropoxy)-5-(4,4,5,5-tetramethyl-1,3,2-dioxaborolan-2-yl)pyrimidine

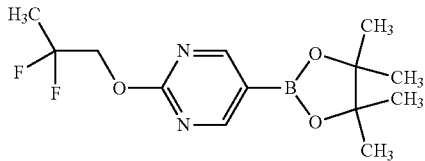 [SMILES: CC(F)(F)COc1ncc(B2OC(C)(C)C(C)(C)O2)cn1]

A mixture of 9.7 g (100.6 mmol) 2,2-difluoropropan-1-ol and THF is cooled to 0° C. and 4.1 g (92.9 mmol) 60% NaH are added in small portions. The reaction mixture is allowed to reach RT and stirred for 1 h, then cooled to 0° C. and 15.0 g (77.4 mmol) 2-chloro-5-bromo-pyrimidine in THF is added. The reaction mixture is stirred for 2 h at RT and then diluted with water and EtOAc. The organic phase is dried and evaporated. The residue is purified by FC giving rise to 17.3 g 5-bromo-2-(2,2-difluoropropoxy)pyrimidine.

The mixture of 9.5 g (37.5 mmol) 5-bromo-2-(2,2-difluoropropoxy)pyrimidine, 12.4 g (48.8 mmol) bis(pinacolato)diborone, 9.6 g (95.5 mmol) KOAc, 0.9 g (1.1 mmol) Pd(dppf)Cl$_2$*DCM and dioxane is heated to 100° C. for 5 h. After cooling to RT, the reaction mixture is diluted with water and EtOAc. To the organic phase, charcoal, NaSO$_4$ and silica gel is added and the mixture is filtered through celite. The filtrate is evaporated and the residue is triturated with petrol ether, filtered and dried.

Yield: 9.5 g (84%), ESI-MS: m/z=301 (M+H)$^+$, R$_t$(HPLC): 0.41 min (HPLC-B)

IV.7 3-[[5-(4,4,5,5-tetramethyl-1,3,2-dioxaborolan-2-yl)pyrimidin-2-yl]oxymethyl]isoxazole

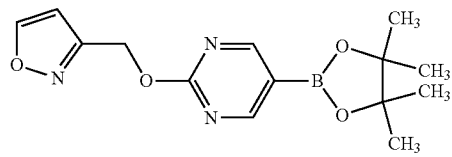 [SMILES: CC1(C)OB(c2cnc(OCc3ccon3)nc2)OC1(C)C]

A mixture of 10.0 g (100.9 mmol) isoxazol-3-ylmethanol and THF is cooled to 0° C. and 4.0 g (100.9 mmol) 60% NaH are added in small portions. The reaction mixture is stirred for 45 min, and then 16.4 g (84.6 mmol) 2-chloro-5-bromo-pyrimidine in DMF is added. The reaction mixture is stirred for 45 min at RT, then cooled to 0° C. and diluted with water. The precipitate is filtered off, washed with water and dried yielding 20.1 g 3-[(5-bromopyrimidin-2-yl)oxymethyl]isoxazole.

The mixture of 20.1 g (78.5 mmol) 3-[(5-bromopyrimidin-2-yl)oxymethyl]isoxazole, 26.2 g (102.1 mmol) bis(pinacolato)diborone, 20.0 g (204.2 mmol) KOAc, 1.6 g (2.0 mmol) Pd(dppf)Cl$_2$*DCM and dioxane is heated to 100° C. for 30 min. After cooling to RT, the reaction mixture is diluted with water and extracted with EtOAc. The organic phases are pooled, charcoal is added and the mixture is filtered. The filtrate is evaporated and the residue is triturated with n-heptane, filtered and dried.

Yield: 17.5 g (74%), ESI-MS: m/z=304 (M+H)$^+$, R$_t$(HPLC): 0.61 min (HPLC-A)

IV.8 [2-[(1-fluorocyclopropyl)methoxy]pyrimidin-5-yl]boronic acid

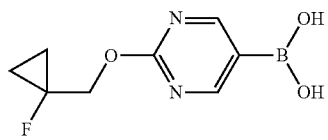 [SMILES: OB(O)c1cnc(OCC2(F)CC2)nc1]

A mixture of 391 mg (4.3 mmol) (1-fluorocyclopropyl)methanol and THF is cooled to 0° C. and 174 mg (4.3 mmol) 60% NaH are added in small portions. The reaction mixture is stirred for 30 min, and then 700 mg (3.6 mmol) 2-chloro-5-bromo-pyrimidine in DMF is added. The reaction mixture is stirred for 30 min at RT, then diluted with water and extracted with DCM. The organic phases are pooled, dried and evaporated furnishing 856 mg 5-bromo-2-[(1-fluorocyclopropyl)methoxy]pyrimidine.

The mixture of 428 mg (1.7 mmol) 5-bromo-2-[(1-fluorocyclopropyl)methoxy]-pyrimidine, 578 mg (2.3 mmol) bis(pinacolato)diborone, 442 mg (4.5 mmol) KOAc, 142 g (0.2 mmol) Pd(dppf)Cl$_2$*DCM and dioxane is heated to 100° C. for 1 h. After cooling to RT, the reaction mixture is diluted with water and extracted with EtOAc. The organic phases are pooled, dried and evaporated Yield: 370 mg, ESI-MS: m/z=213 (M+H)$^+$, R$_t$(HPLC): 0.71 min (HPLC-A)

IV.9 5-(4,4,5,5-tetramethyl-1,3,2-dioxaborolan-2-yl)-2-(4,4,4-trifluorobutoxy)pyrimidine

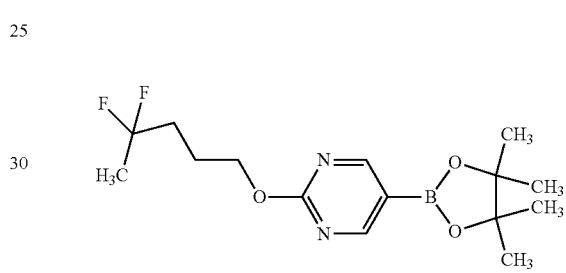

A mixture of 3.5 g (27.5 mmol) 4,4,4-trifluorobutan-1-ol, 4.8 g (25.0 mmol) 2-chloro-5-bromo-pyrimidine, 12.2 g (37.5 mmol) Cs$_2$CO$_3$ is stirred for 2 h at RT, then heated to 50° C. for 8 h then cooled to RT and stirred overnight. The mixture is diluted with ice cold water and the precipitate is filtered off and washed with water, then dissolved in EtOAc, washed with brine, dried and evaporated. The residue is triturated with heptane at 0° C. filtered and dried, giving rise to 5.0 g 5-bromo-2-(4,4,4-trifluorobutoxy)pyrimidine.

The mixture of 3.0 g (10.5 mmol) 5-bromo-2-(4,4,4-trifluorobutoxy)pyrimidine, 3.5 g (13.7 mmol) bis(pinacolato)diborone, 2.7 g (27.4 mmol) KOAc, 0.3 g (0.3 mmol) Pd(dppf)Cl$_2$*DCM and dioxane is heated to 100° C. for 5 h. After cooling to RT, the reaction mixture is diluted with water and EtOAc. To the organic phase, charcoal and NaSO$_4$ is added and the mixture is filtered through celite. The filtrate is evaporated and the residue is triturated with petrol ether, filtered and dried.

Yield: 3.0 g (86%), R$_t$(HPLC): 0.85 min (HPLC-A)

The following Intermediates are obtained in similar manner as described for IV.3 (A), IV.2 (B), IV.6 (C) given in column GP. Details are given in the column synthesis comment, the retention-time and mass (ESI-MS m/z M+H$^+$) determined by HPLC-MS are given in the columns MS and R$_t$.

| IV | Structure | GP | MS | $R_t$ | Synthesis Comment |
|---|---|---|---|---|---|
| IV.25 | 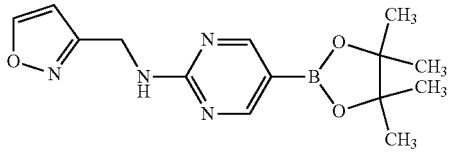 | B | 221 | 0.26 min HPLC-B | 1 h 90° C. |
| IV.26 | 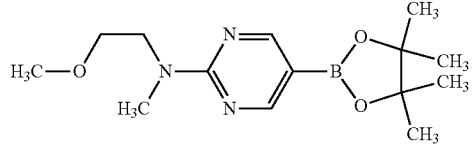 | A | 294 | 0.26 min HPLC-A | 100° C. |
| IV.27 | 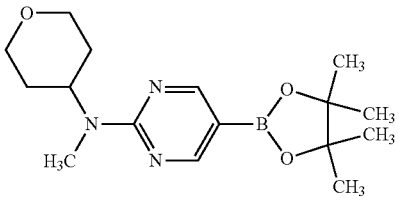 [SMILES: CN(c1ncc(B2OC(C)(C)C(C)(C)O2)cn1)C1CCOCC1] | B | 320 | 0.74 min HPLC-A | 1 h 100° C. |
| IV.28 | 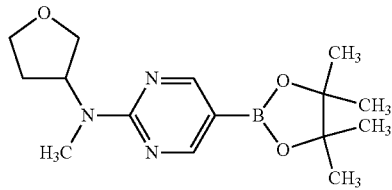 | B | 224 | 0.26 min HPLC-B | 3 h 100° C. |
| IV.29 | 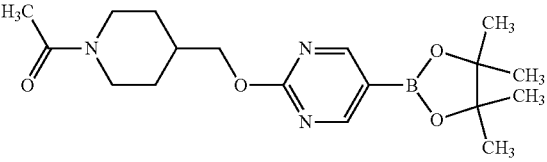 | C | | | TLC: DCM/MeOH 20:1 $R_f$ = 0.4 |
| IV.30 | 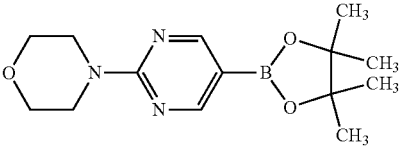 | A | 292 | | TLC: PE/EtOAc 3:1 $R_f$ = 0.4 |
| IV.31 | 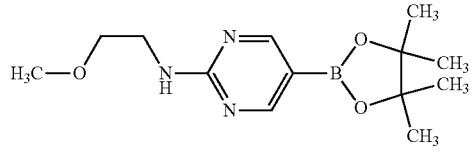 | A | 280 | 0.67 min HPLC-C | 3 h 100° C. |
| IV.32 | 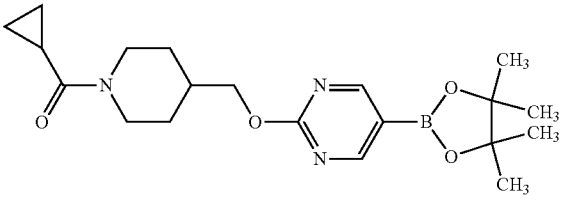 [SMILES: CC1(C)OB(c2cnc(OCC3CCN(C(=O)C4CC4)CC3)nc2)OC1(C)C] | C | 388 | 0.37 min HPLC-D | 1 h 95° C. |

The following Intermediates are commercially available or can be obtained according to the given references.

| # | Structure/Reference |
|---|---|
| IV.50 | 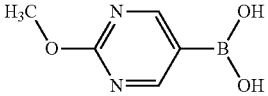<br>J. Med. Chem., 2010, Vol. 53, # 1, 77 |
| IV.51 | 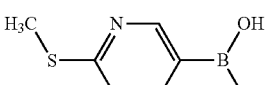<br>Bioorg. Med. Chem. Lett, 2010, vol. 20, # 23, 7046 |
| IV.52 | 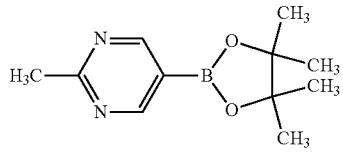<br>J. Am. Chem. Soc., 2014, Vol. 136, # 11, 4287 |
| IV.53 | 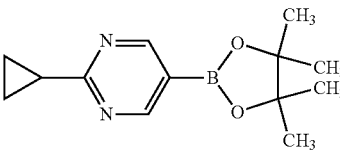<br>Ark Pharm, Inc., 1840 Industrial Drive, Suite 120, Libertyville, IL 60048, USA |

General Procedure A.1

$1^{st}$ step substitution (S):1.0 eq intermediate I given eq intermediate IV and 3 eq DBU in DCM are added. The mixture is held at the given temperature for the given time.

$2^{nd}$ step deprotection (D): 40 eq TFA are added and the mixture is held at the given temperature for the given time, then evaporated and purified by HPLC.

$3^{rd}$ step acylguanidine formation (A): To a mixture of 1.0 eq benzyl alcohol intermediate and DMF 2.0 eq CDI is added and the reaction mixture is stirred overnight. Then 2.0 eq guanidine carbonate are added and the mixture is stirred at RT for the given time. The reaction mixture is diluted with MeOH, DMF and acidified with TFA, filtered and purified by HPLC.

General Procedure A.2

$1^{st}$ step substitution (S): A mixture of 1.1 eq alcohol or intermediate II and THF 1.1 eq 60% NaH is added and the mixture is stirred for 10 min. 1.0 eq intermediate I is added and the mixture is held at the given temperature for the given time, then diluted with water and extracted with EtOAc. The organic phases are pooled, washed with water and brine and evaporated.

$2^{nd}$ step deprotection (D): The intermediate from step 1 is dissolved in THF and 1.5 eq TBAF in THF is added and the mixture is held at the given temperature for the given time, then diluted with water and extracted with EtOAc. The organic phases are pooled, washed with water and brine and evaporated.

$3^{rd}$ step acylguanidine formation (A): To a mixture of 1.0 eq benzyl alcohol intermediate from step 2 and DMF 1.5 eq CDI is added and the reaction mixture is stirred for 1 h at RT. Then 2.0 eq guanidine carbonate are added and the mixture is stirred at RT for the given time. The reaction mixture is acidified with TFA, filtered and purified by HPLC.

General Procedure A.3

A mixture of 5.0 eq nucleophile and THF is cooled to 0° C. and 3 eq 60% NaH is added, then warmed to RT and 1.0 eq of intermediate III dissolved in DMF is added and the mixture held at the given temperature for the given time. The reaction mixture is concentrated and diluted with water. The precipitate is filtered, washed and dried. Alternatively the crude product is purified by HPLC after concentration.

General Procedure B.1

$1^{st}$ step coupling (C):1.0 eq intermediate I, 1.0 eq intermediate IV and 2.0 eq 2M $Na_2CO_3$ solution 0.10 eq bis(triphenylphosphine)palladium(II)chloride in dioxane are heated to the given temperature for the given time. The resulting benzyl alcohol intermediate is purified by FC or HPLC.

$2^{nd}$ step acylguanidine formation (A): To a mixture of 1.0 eq benzyl alcohol intermediate and DMF 1.5 eq CDI is added and the reaction mixture is stirred for 2 h at RT. Then 2.0 eq guanidine carbonate are added and the mixture is stirred at RT for the given time. The reaction mixture is diluted with MeOH, DMF and acidified with TFA, filtered and purified by HPLC.

General Procedure B.2

1.0 eq of intermediate III 1.1 eq intermediate IV and 3.5 eq $K_3PO_4$ 0.1 eq XPhos Pd G2 in dioxane are heated to the given temperature for the given time. The reaction mixture is filterd through a Thiol-MP SPE cartridge and purified by HPLC.

General Procedure B.3

1.0 eq of intermediate III 1.5 eq intermediate IV and 3.0 eq $K_3PO_4$ 0.05 eq XPhos Pd G2 in dioxane/water (ca. 5:1) are heated to the given temperature for the given time. The reaction mixture is purified by HPLC.

The following examples in table 3 (example number given in column #) are prepared according to general procedures A or B and as described below. Details for the general procedures are given in the column synthesis comment, the retention-time and mass (ESI-MS m/z M+H$^+$) determined by HPLC-MS are given in the columns RT and MS.

TABLE 3

| # | Structure | GP | starting material | R$_t$ [min] (HPLC method) | MS | Synthesis Comment |
|---|---|---|---|---|---|---|
| 01 | 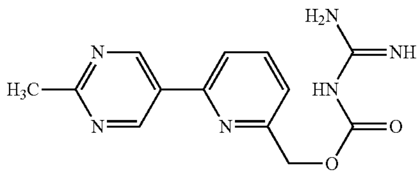 [SMILES: Cc1ncc(-c2cccc(COC(=O)NC(=N)N)n2)cn1] | B.3 | III.1 IV.52 | 0.31 (B) | 287 | 2 h, 100° C. |
| 02 | 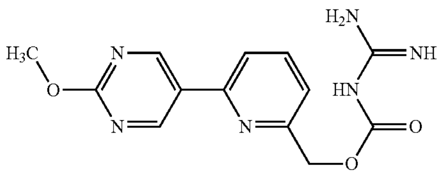 [SMILES: COc1ncc(-c2cccc(COC(=O)NC(=N)N)n2)cn1] | B.1 | III.50 IV.50 | 0.34 (B) | 303 | C: 1 h, 100° C. A: 2 eq guanidine carbonate, 1.1 eq CDI, 48 h |
| 03 | 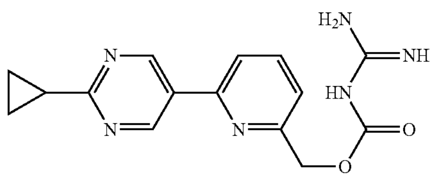 [SMILES: N=C(N)NC(=O)OCc1cccc(-c2cnc(C3CC3)nc2)n1] | B.3 | III.1 IV.53 | 0.38 (B) | 313 | 2 h, 100° C. |
| 04 | 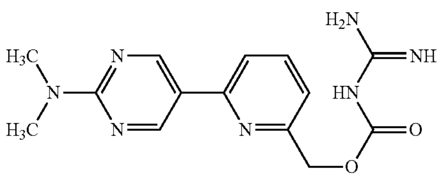 [SMILES: CN(C)c1ncc(-c2cccc(COC(=O)NC(=N)N)n2)cn1] | B.3 | III.1 IV.3 | 0.68 (A) | 316 | 2 h, 100° C. |
| 05 | 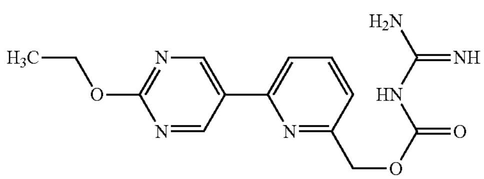 | A.1 | I.1 ethanol | 0.75 (A) | 317 | S: overnight, RT D: 2 h, RT A: 3 h, RT |
| 06 | 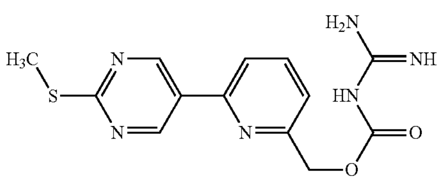 [SMILES: CSc1ncc(-c2cccc(COC(=O)NC(=N)N)n2)cn1] | B.3 | III.1 IV.51 | 0.77 (A) | 319 | 1 h, 100° C. |
| 07 | 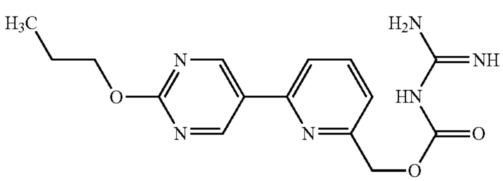 [SMILES: CCCOc1ncc(-c2cccc(COC(=O)NC(=N)N)n2)cn1] | A.1 | I.1 1-propanol | 0.51 (F) | 331 | S: overnight, RT D: 3 h, RT A: 3 h, RT |
| 08 | 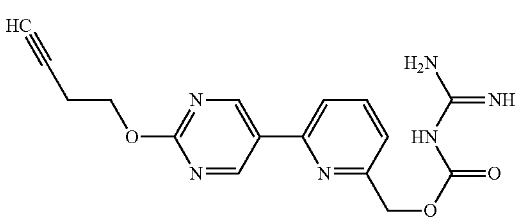 [SMILES: C#CCCOc1ncc(-c2cccc(COC(=O)NC(=N)N)n2)cn1] | A.1 | I.1 but-3-yn-1-ol | 0.47 (F) | 341 | S: overnight, RT D: 3 h, RT A: 3 h, RT |

TABLE 3-continued

| # | Structure | GP | starting material | R$_t$ [min] (HPLC method) | MS | Synthesis Comment |
|---|---|---|---|---|---|---|
| 09 | 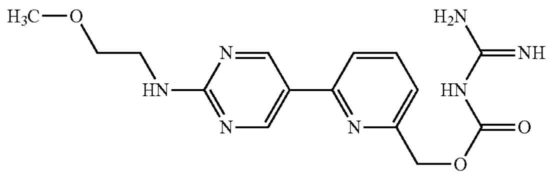 [SMILES: COCCNc1ncc(-c2cccc(COC(=O)NC(=N)N)n2)cn1] | B.3 | III.1 IV.31 | 0.69 (A) | 346 | 1.5 h, 100° C. |
| 10 | 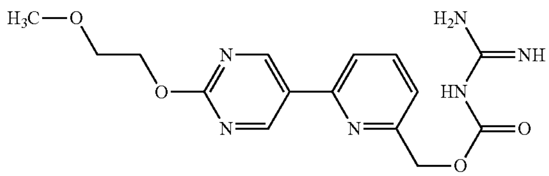 | A.1 | I.1 2-methoxy-ethanol | 0.41 (H) | 347 | S: 4 d, RT D: 1 h, RT A: 3 h, RT |
| 11 | 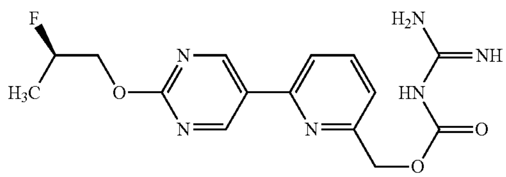 [SMILES: C[C@@H](F)COc1ncc(-c2cccc(COC(=O)NC(=N)N)n2)cn1] | A.1 | I.1 (2R)-2-fluoro-propan-1-ol | 0.47 (F) | 349 | S: 84 h, RT D: 3 h, RT A: 2 h, RT |
| 12 | 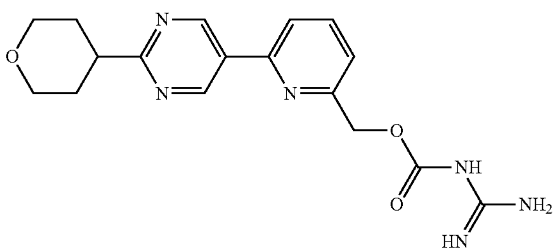 [SMILES: N=C(N)NC(=O)OCc1cccc(-c2cnc(C3CCOCC3)nc2)n1] | B.3 | III.1 IV.4 | 0.36 (B) | 357 | 3 h, 100° C. |
| 13 | 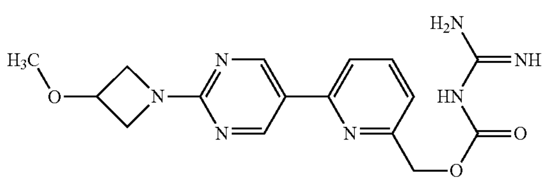 [SMILES: COC1CN(c2ncc(-c3cccc(COC(=O)NC(=N)N)n3)cn2)C1] | B.1 | III.50 IV.1 | 0.69 (A) | 358 | C: 1.5 h, 100° C. A: overnight |
| 14 | 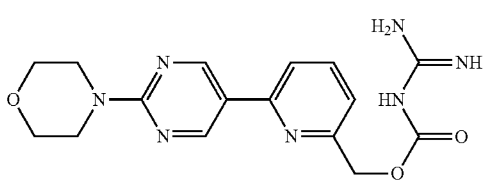 [SMILES: N=C(N)NC(=O)OCc1cccc(-c2cnc(N3CCOCC3)nc2)n1] | B.1 | III.50 IV.30 | 0.38 (B) | 358 | C: 3 eq Na$_2$CO$_3$, 100° C. 3 h A: overnight |
| 15 | 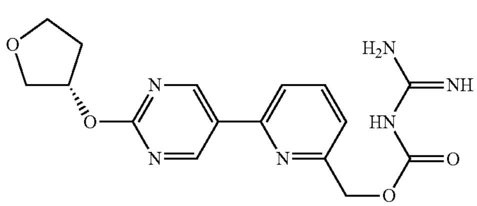 [SMILES: N=C(N)NC(=O)OCc1cccc(-c2cnc(O[C@H]3CCOC3)nc2)n1] | A.1 | I.1 (3S)-tetrahydro-furan-3-ol | 0.42 (H) | 359 | S: 4 d, RT D: 1 h, RT A: 3 h, RT |
| 16 | 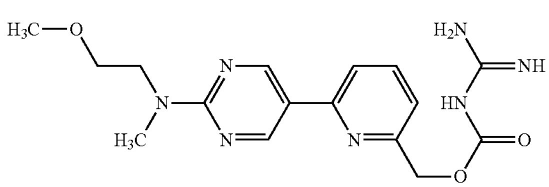 [SMILES: COCCN(C)c1ncc(-c2cccc(COC(=O)NC(=N)N)n2)cn1] | B.3 | III.1 IV.26 | 0.4 (A) | 360 | 1.5 h, 100° C. |

TABLE 3-continued

| # | Structure | GP | starting material | R$_t$ [min] (HPLC method) | MS | Synthesis Comment |
|---|---|---|---|---|---|---|
| 17 | 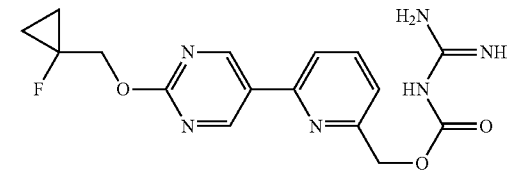 [SMILES: N=C(N)NC(=O)OCc1cccc(-c2cnc(OCC3(F)CC3)nc2)n1] | A.1 | I.1 (1-fluoro-cyclo-propyl)-methanol | 0.5 (F) | 361 | S: overnight, RT D: 3 h, RT A: 3 h, RT |
| 18 | 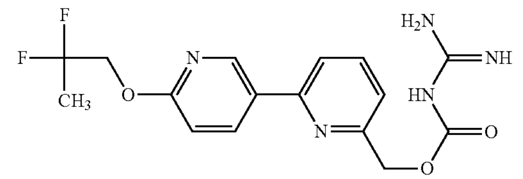 [SMILES: CC(F)(F)COc1ccc(-c2cccc(COC(=O)NC(=N)N)n2)cn1] | A.3 | I.3 2,2-difluoro-propan-1-ol | 0.49 (B) | 366 | overnight, RT |
| 19 | 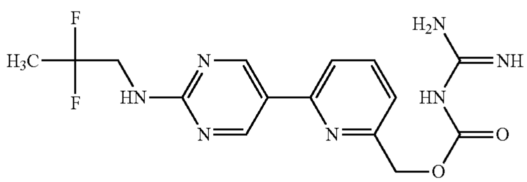 [SMILES: CC(F)(F)CNc1ncc(-c2cccc(COC(=O)NC(=N)N)n2)cn1] | B.2 | III.1 IV.2 | 0.4 (B) | 366 | 3 h, 90° C. |
| 20 | 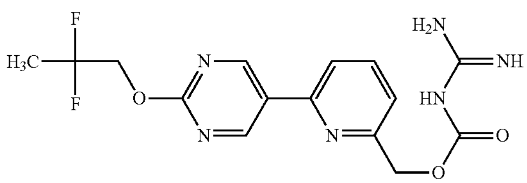 [SMILES: CC(F)(F)COc1ncc(-c2cccc(COC(=O)NC(=N)N)n2)cn1] | A.1 | I.1 2,2-difluoro-propan-1-ol | 0.52 (H) | 367 | S: 4 d, RT D: 1 h, RT A: 3 h, RT |
| 21 | 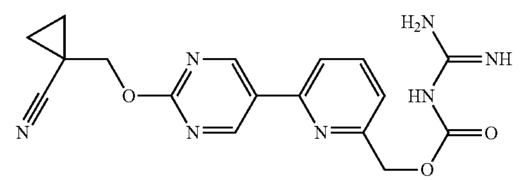 [SMILES: N#CC1(COc2ncc(-c3cccc(COC(=O)NC(=N)N)n3)cn2)CC1] | A.2 | I.2 II.51 | 0.39 (B) | 368 | S: 3 h, RT D: overnight, RT A: overnight |
| 22 | 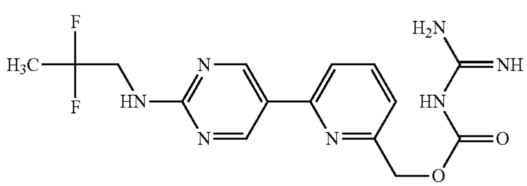 [SMILES: CC(F)(F)CNc1ncc(-c2cccc(COC(=O)NC(=N)N)n2)cn1] | B.2 | III.1 IV.25 | 0.35 (B) | 369 | 3 h, 90° C. |
| 23 | 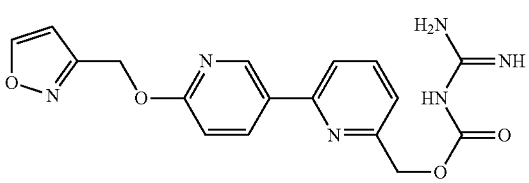 [SMILES: N=C(N)NC(=O)OCc1cccc(-c2ccc(OCc3ccon3)nc2)n1] | A.3 | I.3 isoxazol-3-ylmethanol | 0.51 (E) | 369 | overnight, RT |
| 24 | 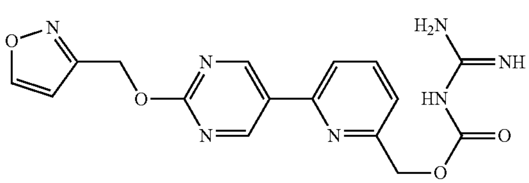 [SMILES: N=C(N)NC(=O)OCc1cccc(-c2cnc(OCc3ccon3)nc2)n1] | A.1 | I.1 isoxazol-3-ylmethanol | 0.45 (H) | 370 | S: 4 d, RT D: 1 h, RT A: 3 h, RT |

TABLE 3-continued

| # | Structure | GP | starting material | R$_t$ [min] (HPLC method) | MS | Synthesis Comment |
|---|---|---|---|---|---|---|
| 25 | 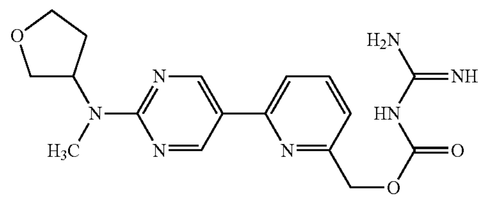 [SMILES: CN(c1ncc(-c2cccc(COC(=O)NC(=N)N)n2)cn1)C1CCOC1] | B.3 | III.1 IV.28 | 0.75 (A) | 372 | 1.5 h, 100° C. |
| 26 | 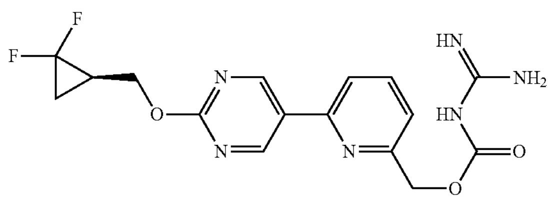 [SMILES: N=C(N)NC(=O)OCc1cccc(-c2cnc(OC[C@H]3CC3(F)F)nc2)n1] | A.1 | I.1 [(1R)-2,2-difluoro-cyclo-propyl]-methanol | 0.53 (F) | 379 | S: overnight, RT D: 3 h, RT A: 3 h, RT |
| 27 | 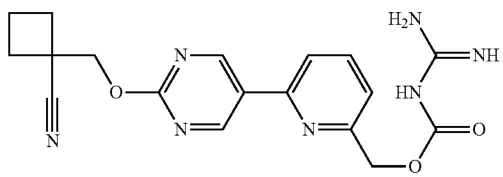 [SMILES: N#CC1(COc2ncc(-c3cccc(COC(=O)NC(=N)N)n3)cn2)CCC1] | A.1 | I.1 1-(hydroxy-methyl)-cyclo-butane-carbo-nitrile | 0.56 (G) | 382 | S: overnight, RT D: 3 h, RT A: 3 h, RT |
| 28 | 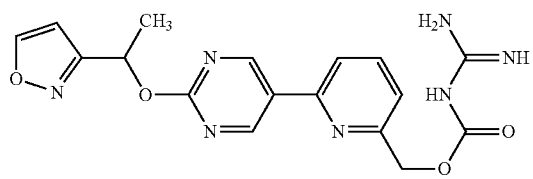 [SMILES: CC(Oc1ncc(-c2cccc(COC(=O)NC(=N)N)n2)cn1)c1ccon1] | A.2 | I.2 II.50 | 0.41 (B) | 384 | S: 3 h, RT D: overnight, RT A: overnight |
| 29 | 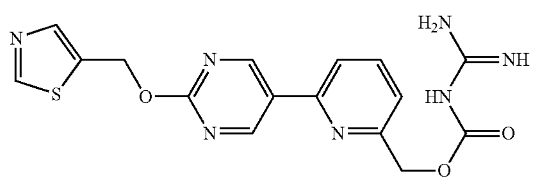 [SMILES: N=C(N)NC(=O)OCc1cccc(-c2cnc(OCc3cncs3)nc2)n1] | A.1 | I.1 thiazol-5-yl-methanol | 0.43 (F) | 386 | S: 84 h, RT D: 3 h, RT A: 2 h, RT |
| 30 | 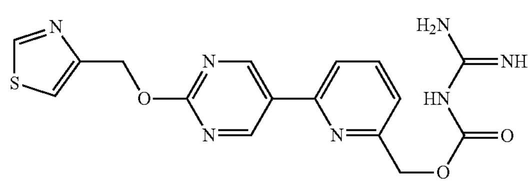 [SMILES: N=C(N)NC(=O)OCc1cccc(-c2cnc(OCc3cscn3)nc2)n1] | A.1 | I.1 thiazol-4-yl-methanol | 0.43 (F) | 386 | S: 84 h, RT D: 3 h, RT A: 2 h, RT |
| 31 | 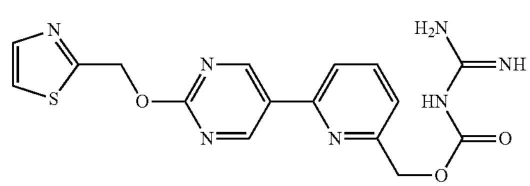 [SMILES: N=C(N)NC(=O)OCc1cccc(-c2cnc(OCc3nccs3)nc2)n1] | A.1 | I.1 thiazol-2-ylmethanol | 0.45 (F) | 386 | S: 84 h, RT D: 3 h, RT A: 2 h, RT |
| 32 | 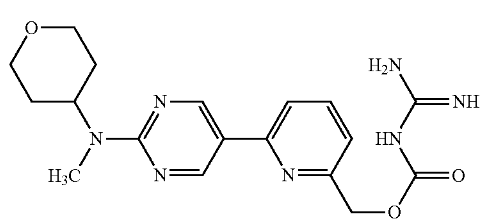 [SMILES: CN(c1ncc(-c2cccc(COC(=O)NC(=N)N)n2)cn1)C1CCOCC1] | B.3 | III.1 IV.27 | 0.76 (A) | 386 | 1 h, 100° C. |

TABLE 3-continued

| # | Structure | GP | starting material | $R_t$ [min] (HPLC method) | MS | Synthesis Comment |
|---|---|---|---|---|---|---|
| 33 | 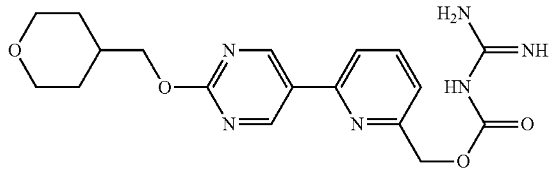 [SMILES: N=C(N)NC(=O)OCc1cccc(-c2cnc(OCC3CCOCC3)nc2)n1] | A.1 | I.1 tetra-hydro-pyran-4-ylmethanol | 0.48 (H) | 387 | S: 4 d, RT D: 1 h, RT A: 3 h, RT |
| 34 | 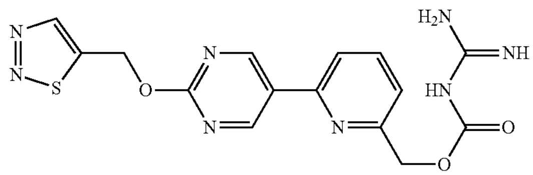 [SMILES: N=C(N)NC(=O)OCc1cccc(-c2cnc(OCc3cnns3)nc2)n1] | A.1 | I.1 thiadiazol-5-ylmethanol | 0.44 (F) | 387 | S: 84 h, RT D: 3 h, RT A: 2 h, RT |
| 35 | 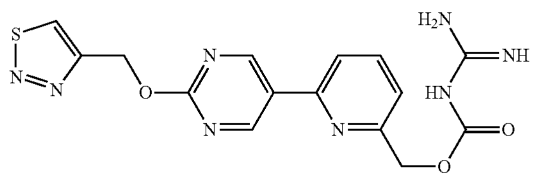 [SMILES: N=C(N)NC(=O)OCc1cccc(-c2cnc(OCc3csnn3)nc2)n1] | A.1 | I.1 thiadiazol-4-ylmethanol | 0.43 (F) | 387 | S: 84 h, RT D: 3 h, RT A: 2 h, RT |
| 36 | 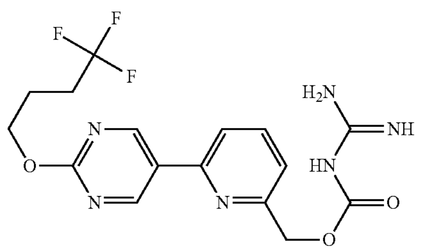 [SMILES: N=C(N)NC(=O)OCc1cccc(-c2cnc(OCCCC(F)(F)F)nc2)n1] | A.1 | I.1 4,4,4-trifluoro-butan-1-ol | 0.58 (F) | 399 | S: overnight, RT D: 3 h, RT A: 3 h, RT |
| 37 | 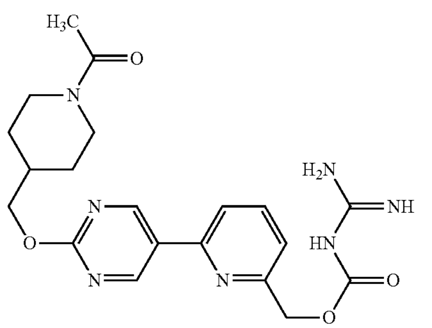 [SMILES: CC(=O)N1CCC(COc2ncc(-c3cccc(COC(=O)NC(=N)N)n3)cn2)CC1] | B.1 | III.50 IV.29 | 0.38 (B) | 428 | C: 3 eq Na$_2$CO$_3$, 100° C. 3 h A: overnight |
| 38 | 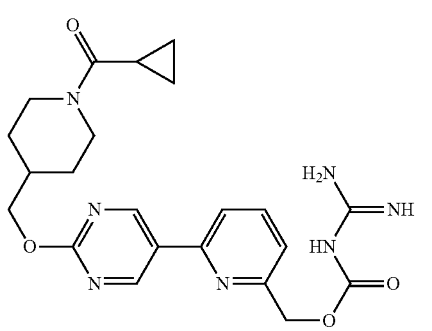 [SMILES: N=C(N)NC(=O)OCc1cccc(-c2cnc(OCC3CCN(C(=O)C4CC4)CC3)nc2)n1] | B.2 | III.1 IV.32 | 0.42 (D) | 454 | 1 h 80° C. |

EXAMPLE 03

[6-(2-cyclopropylpyrimidin-5-yl)-2-pyridyl]methyl N-carbamimidoylcarbamate

A mixture of 1.0 eq of intermediate III.1, 1.1 eq intermediate IV.53, 3.0 eq $K_3PO_4$ and 0.07 eq XPhos Pd G2 in dioxane/water (ca. 5:1) are heated to 100° C. for 2 h. After cooling to RT the solvent is evaporated in taken up in a mixture of MeOH and DCM, filtered through a PL-thiol cartridge and evaporated. The crude product is purified by HPLC.

ESI-MS: m/z=313 $(M+H)^+$, $R_f$(HPLC): 0.39 min (HPLC-B)

EXAMPLE 07

[6-(2-propoxypyrimidin-5-yl)-2-pyridyl]methyl N-carbamimidoylcarbamate

A gentle stream of argon is passed through a mixture of 1.0 eq of intermediate III.1, 1.1 eq intermediate IV.5 and 2.5 eq $K_3PO_4$ in dioxane/water (ca. 5:1). Then 0.1 eq XPhos Pd G2 are added and the mixture heated to 100° C. for 1 h. After cooling to RT the solvent is evaporated and the crude product is purified by FC.

ESI-MS: m/z=331 $(M+H)^+$, $R_f$(HPLC): 0.81 min (HPLC-A)

EXAMPLE 08

[6-(2-but-3-ynoxypyrimidin-5-yl)-2-pyridyl]methyl N-carbamimidoylcarbamate 3.0 eq DBU are added to a mixture of 3.0 eq 3-butyn-1-ol and DCM. After 1 h at RT, 1.0 eq of intermediate I.1 in DCM is added and the mixture is stirred at RT for 3 h, then diluted with DCM and washed with $NaHCO_3$ solution and brine, dried and evaporated. Giving rise to crude tert-butyl-[[6-(2-but-3-ynoxypyrimidin-5-yl)-2-pyridyl]methoxy]-dimethyl-silane (ESI-MS: m/z=370 $(M+H)^+$, $R_f$(HPLC): 1.26 min (HPLC-C)). THF and 1.5 eq TBAF are added and the mixture is stirred at RT for 20 min. The solvent is evaporated and the residue purified by FC, giving rise to [6-(2-but-3-ynoxypyrimidin-5-yl)-2-pyridyl]methanol (ESI-MS: m/z=256 $(M+H)^+$, $R_f$(HPLC): 0.80 min (HPLC-C)).

To a mixture of 1.0 eq [6-(2-but-3-ynoxypyrimidin-5-yl)-2-pyridyl]methanol and DMF, 1.5 eq CDI is added and the mixture is stirred for 2 h at RT, then 2.0 eq guanidine carbonate are added and stirring is continued overnight and then diluted with water. The precipitate is filtered off and dried, triturated with ether and filtered, then with MeOH and filtered and dried.

ESI-MS: m/z=341 $(M+H)^+$, $R_f$(HPLC): 0.79 min (HPLC-C)

EXAMPLE 17

[6-[2-[(1-fluorocyclopropyl)methoxy]pyrimidin-5-yl]-2-pyridyl]-methyl N-carbamimidoylcarbamate A gentle stream of argon is passed through a mixture of 1.0 eq intermediate III.1, 1.11 eq intermediate IV.8 and 2.0 eq $K_3PO_4$ in dioxane/water (ca. 5:1). Then 0.1 eq XPhos Pd G2 are added and the mixture heated to 100° C. for 30 min. After cooling to RT the reaction mixture is diluted with water and extracted with EtOAc. The organic phases are pooled, dried and evaporated and the crude product is purified by FC.

ESI-MS: m/z=361 $(M+H)^+$, $R_f$(HPLC): 0.75 min (HPLC-A)

EXAMPLE 20

[6-[2-(2,2-difluoropropoxy)pyrimidin-5-yl]-2-pyridyl]methyl N-carbamimidoylcarbamate A mixture of 1.0 eq (6-bromo-2-pyridyl)methanol, 1.1 eq intermediate IV.6 and 2.5 eq $K_3PO_4$ in dioxane/water (ca. 5:1) and 0.05 eq XPhos Pd G2 is heated to 100° C. for 1 h. After cooling to RT the organic phases is separated and evaporated. The resulting crude product is purified by FC, furnishing [6-[2-(2,2-difluoropropoxy)pyrimidin-5-yl]-2-pyridyl]methanol (ESI-MS: m/z=282 $(M+H)^+$, $R_f$(HPLC): 0.85 min (HPLC-A)).

To a mixture of 1.0 eq [6-[2-(2,2-difluoropropoxy)pyrimidin-5-yl]-2-pyridyl]methanol and DMF, 1.5 eq CDI is added and the mixture is stirred for 2 h at RT, then 2.0 eq guanidine carbonate are added and stirring is continued overnight and then diluted with ice-cold water. The precipitate is filtered off and recrystallized from 95% EtOH, filtered off and dried.

ESI-MS: m/z=367 $(M+H)^+$, $R_f$(HPLC): 0.80 min (HPLC-A), mp: 195° C., $R_f$(TLC): 0.20 (DCM/MeOH/$NH_4OH$ 9:1:0.01)

EXAMPLE 24

[6-[2-(isoxazol-3-ylmethoxy)pyrimidin-5-yl]-2-pyridyl]methyl N-carbamimidoylcarbamate A mixture of 1.0 eq intermediate III.1, 1.10 eq intermediate IV.7, 2.0 eq $K_3PO_4$ and 0.1 eq XPhos Pd G2 in dioxane/water (ca. 5:1) is heated to 100° C. for 30 min. After cooling to RT the reaction mixture is diluted with water and extracted with EtOAc. The organic phases are pooled, dried and evaporated and the crude product is purified by FC, then triturated with ether, filtered and dried.

ESI-MS: m/z=370 $(M+H)^+$, $R_f$(HPLC): 0.75 min (HPLC-C), mp: 183° C., $R_f$(TLC): 0.18 (DCM/MeOH 9:1)

EXAMPLE 26

[6-[2-[[(1R)-2,2-difluorocyclopropyl]methoxy]pyrimidin-5-yl]-2-pyridyl]methyl N-carbamimidoylcarbamate 3.0 eq DBU are added to a mixture of 3.0 eq [(1R)-2,2-difluorocyclopropyl]methanol and DCM. After 1.5 h at RT, 1.0 eq of intermediate 1.1 is added and the mixture is stirred at RT overnight. The intermediate tert-butyl-[[6-[2-[[(1R)-2,2-difluorocyclopropyl]-methoxy]pyrimidin-5-yl]-2-pyridyl]methoxy]-dimethyl-silane (ESI-MS: m/z=408 $(M+H)^+$, $R_f$(HPLC): 1.33 min (HPLC-A)) is not isolated. 45 eq TFA are added to the reaction mixture and stirring is continued for 2 h at RT. The solvent is evaporated and the residue purified by HPLC, giving rise to [6-[2-[[(1R)-2,2-difluorocyclopropyl]-methoxy]-pyrimidin-5-yl]-2-pyridyl]methanol (ESI-MS: m/z=294 $(M+H)^+$, $R_f$(HPLC): 0.86 min (HPLC-A)).

To a mixture of 1.0 eq [6-[2-[[(1R)-2,2-difluorocyclopropyl]methoxy]pyrimidin-5-yl]-2-pyridyl]methanol and DMF, 1.44 eq CDI is added and the mixture is stirred at RT overnight, then 1.44 eq guanidine carbonate are added and stirring is continued for 3h. The reaction mixture is diluted with water and stirred for 2 h. The precipitate is filtered off and dried.

ESI-MS: m/z=379 (M+H)$^+$, R$_f$(HPLC): 0.82 min (HPLC-A) mp: 193-196° C., R$_f$(TLC): 0.30 (DCM/MeOH/NH$_4$OH 9:1:0.01)

EXAMPLE 36

[6-[2-(4,4,4-trifluorobutoxy)pyrimidin-5-yl]-2-pyridyl]methyl N-carbamimidoylcarbamate A mixture of 1.0 eq (6-bromo-2-pyridyl)methanol, 1.1 eq intermediate IV.9 and 2.0 eq K$_3$PO$_4$ in dioxane/water (ca. 5:1) and 0.04 eq XPhos Pd G2 is heated to 100° C. for 1 h. After cooling to RT the mixture is diluted with ice cold water and extracted with EtOAc. The organic phases are pooled washed with brine, dried and evaporated.

The resulting crude product is purified by FC, [6-[2-(4,4,4-trifluorobutoxy)pyrimidin-5-yl]-2-pyridyl]methanol (ESI-MS: m/z=314 (M+H)$^+$, R$_f$(HPLC): 0.91 min (HPLC-A)).

To a mixture of 1.0 eq [6-[2-(4,4,4-trifluorobutoxy)pyrimidin-5-yl]-2-pyridyl]methanol and DMF, 1.5 eq CU is added and the mixture is stirred for 2 h at RT, then 2.0 eq guanidine carbonate are added and stirring is continued for 4 h and then diluted with ice-cold water. The precipitate is filtered off and dried.

ESI-MS: m/z=399 (M+H)$^+$, R$_f$(HPLC): 0.85 min (HPLC-A), mp: 194-197° C., R$_f$(TLC): 0.35 (DCM/MeOH/NH$_4$OH 9:1:0.01)

The invention claimed is:

1. A compound of formula (I)

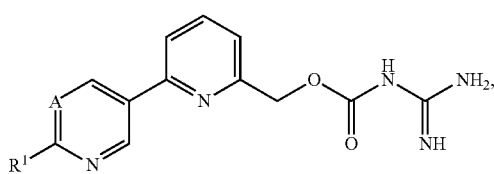

(I)

wherein
A is N or CH;
R$^1$ is selected from the group consisting of C$_{1-6}$-alkyl, C$_{3-6}$-cycloalkyl, heterocyclyl, —O—R$^2$, —S—R$^2$, —NH—R$^2$ and —N(R$^2$)$_2$,
wherein each R$^2$ is independently selected from the group consisting of C$_{1-6}$-alkyl, C$_{3-6}$-cycloalkyl, heterocyclyl, —(C$_{1-2}$-alkyl)-(C$_{3-6}$-cycloalkyl), —(C$_{1-2}$-alkyl)-heterocyclyl, —(C$_{1-2}$-alkyl)-aryl, —(C$_{1-2}$-alkyl)-heteroaryl and —(C$_{1-2}$-alkyl)-C≡CH;
wherein each heterocyclyl of R$^1$ and R$^2$ is a 4- to 7-membered saturated carbocyclic group, in which 1 or 2 CH$_2$-moieties are independently of each other replaced by an atom or group selected from NH, O, S, —S(=O)—, —S(=O)$_2$— or —C(=O)—; and
wherein each aryl is selected from the group consisting of phenyl and naphthyl; and
wherein each heteroaryl is a 5- or 6-membered heteroaromatic ring which contains 1, 2 or 3 heteroatoms independently selected from =N—, —NH—, —O— and —S—, wherein in heteroaromatic groups containing a —CH=N— unit, this group is optionally replaced by —NH—C(=O)—; and
wherein each alkyl, cycloalkyl, heterocyclyl, aryl or heteroaryl group of R$^1$ and R$^2$ is optionally independently substituted with one or more F, Cl, CN, OH, C$_{1-3}$-alkyl, —O—(C$_{1-3}$-alkyl), —C(=O)—(C$_{1-3}$-alkyl) and —C(=O)—(C$_{3-7}$-cycloalkyl);
wherein each of the above-mentioned alkyl groups may be linear or branched and are optionally substituted by one or more F;
or a salt thereof.

2. A compound of formula (I) according to claim 1, wherein R$^1$ is C$_{1-4}$-alkyl, C$_{3-5}$-cycloalkyl, heterocyclyl, —O—R$^2$, —S—R$^2$, —NH—R$^2$ or —N(R$^2$)$_2$;
wherein each heterocyclyl is a 4- to 6-membered saturated carbocyclic group, in which 1 or 2 CH$_2$-moieties are replaced by a heteroatom selected from NH, O or S; and
wherein each alkyl, cycloalkyl or heterocyclyl group is optionally independently substituted with 1 to 5 F and/or 1 to 3 substituents independently selected from the group consisting of Cl, CN, OH, C$_{1-2}$-alkyl, —O—(C$_{1-2}$-alkyl), —C(=O)—(C$_{1-2}$-alkyl) and —C(=O)—(C$_{3-4}$-cycloalkyl);
or a salt thereof.

3. A compound of formula (I) according to claim 2, wherein R$^1$ is C$_{1-2}$-alkyl, C$_{3-4}$-cycloalkyl, heterocyclyl, —O—R$^2$, —NH—R$^2$ or —N(R$^2$)$_2$;
wherein each heterocyclyl is selected from the group consisting of azetidinyl, piperidinyl, tetrahydrofuranyl, tetrahydropyranyl and morpholinyl; and
wherein each alkyl, cycloalkyl or heterocyclyl group is optionally independently substituted with 1 to 3 F or one substituent selected from the group consisting of CN, OH, CH$_3$, —O—CH$_3$, —C(=O)—CH$_3$ and —C(=O)-cyclopropyl;
or a salt thereof.

4. A compound of formula (I) according to claim 1, wherein R$^2$ is selected from the group consisting of C$_{1-4}$-alkyl, C$_{3-5}$-cycloalkyl, heterocyclyl, —(C$_{1-2}$-alkyl)-(C$_{3-5}$-cycloalkyl), —(C$_{1-2}$-alkyl)-heterocyclyl, —(C$_{1-2}$-alkyl)-aryl, —(C$_{1-2}$-alkyl)-heteroaryl and —(C$_{1-2}$-alkyl)-C≡CH;
wherein each heterocyclyl is a 4- to 6-membered saturated carbocyclic group, in which 1 or 2 CH$_2$-moieties are replaced by a heteroatom selected from NH, O or S; and
wherein each aryl is selected from the group consisting of phenyl and naphthyl; and
wherein each heteroaryl is a 5- or 6-membered heteroaromatic ring which contains 1, 2 or 3 heteroatoms independently selected from =N—, —NH—, —O— and —S—; and
wherein each alkyl, cycloalkyl, heterocyclyl, aryl or heteroaryl group is optionally independently substituted with one or more F, Cl, CN, OH, C$_{1-2}$-alkyl, —O—(C$_{1-2}$-alkyl), —C(=O)—(C$_{1-2}$-alkyl) and —C(=O)—(C$_{3-7}$-cycloalkyl);
or a salt thereof.

5. A compound of formula (I) according to claim 1, wherein R$^2$ is selected from the group consisting of: C$_{1-4}$-alkyl, —CH$_2$—(C$_{3-4}$-cycloalkyl), —CH$_2$-heterocyclyl, —CH$_2$-heteroaryl and —CH$_2$—CH$_2$—C≡CH;
wherein each heterocyclyl is selected from the group consisting of tetrahydrofuranyl and piperidinyl; and
wherein each heteroaryl is selected from the group consisting of isoxazolyl, thiazolyl and thiadiazolyl; and wherein each alkyl, cycloalkyl, heterocyclyl, aryl or heteroaryl group is optionally independently substituted with one or more F, CN, CH$_3$, —OCH$_3$, —C(=O)—CH$_3$ and —C(=O)-cyclopropyl;
or a salt thereof.

6. A compound of formula (I) according to claim 1, wherein
A is N;
or a salt thereof.

7. A compound of formula (I) according to claim 1, wherein
A is N; and
R$^1$ is selected from the group consisting of cyclopropyl, heterocyclyl and —O—R$^2$;
wherein R$^2$ is selected from the group consisting of C$_{1-6}$-alkyl, —(C$_{1-2}$-alkyl)-(C$_{3-6}$-cycloalkyl), —(C$_{1-2}$-alkyl)-heteroaryl and —(C$_{1-2}$-alkyl)-C≡CH;
wherein each heterocyclyl is selected from the group consisting of azetidinyl, piperidinyl, tetrahydrofuranyl, tetrahydropyranyl and morpholinyl; and
wherein each heterocyclyl group is optionally independently substituted with one substituent selected from F, CN, OH, CH$_3$, —O—CH$_3$; and
wherein each heteroaryl is selected from the group consisting of isoxazolyl, thiazolyl and thiadiazolyl; and
wherein each alkyl, cycloalkyl, heterocyclyl, or heteroaryl group is optionally independently substituted with one or more F, CN, CH$_3$, —OCH$_3$, —C(=O)—CH$_3$ and —C(=O)-cyclopropyl;
wherein each of the above-mentioned alkyl groups may be linear or branched and are optionally substituted by one or more F;
or a salt thereof.

8. A compound of formula (I) according to claim 1, wherein
A is N;
R$^1$ is selected from the group consisting of cyclopropyl, heterocyclyl and —O—R$^2$;
wherein R$^2$ is selected from the group consisting of C$_{1-4}$-alkyl, —CH$_2$—(C$_{3-4}$-cycloalkyl), —CH$_2$-heteroaryl and —CH$_2$—CH$_2$—C≡CH;
wherein each heteroaryl is selected from the group consisting of isoxazolyl, thiazolyl and thiadiazolyl; and
wherein each alkyl, cycloalkyl, aryl or heteroaryl group is optionally independently substituted with one or more F, CN and —OCH$_3$;
wherein each heterocyclyl is selected from the group consisting of azetidinyl, piperidinyl, tetrahydrofuranyl, tetrahydropyranyl and morpholinyl; and
wherein each heterocyclyl group is optionally independently substituted with one substituent selected from F, CN, OH, CH$_3$, —O—CH$_3$;
or a salt thereof.

9. A compound of formula (I) according to claim 1 selected from the group consisting of:

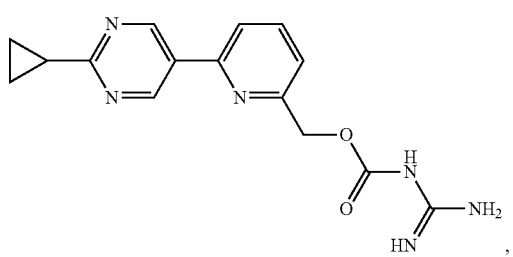

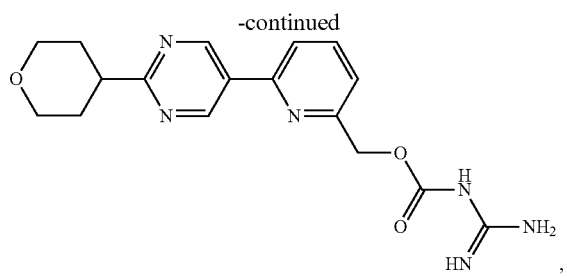

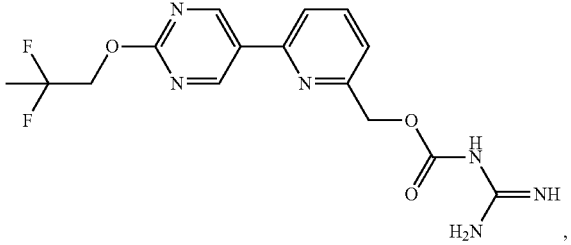

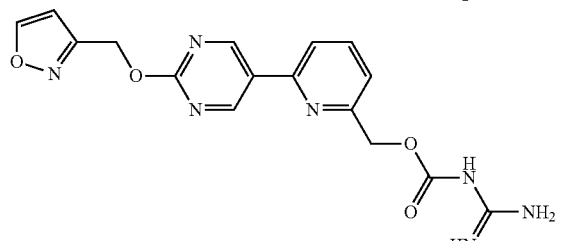

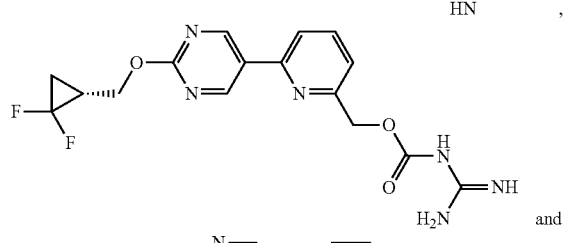

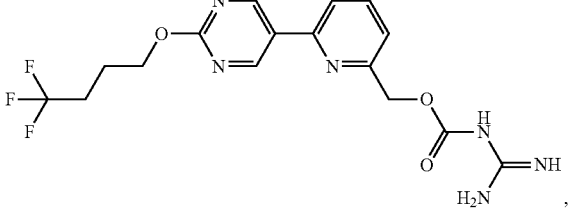

or a salt thereof.

10. A pharmaceutically acceptable salt of a compound according to claim 1.

11. A compound according to claim 1, or a pharmaceutically acceptable salt thereof, for use as a medicament.

12. A method of using a compound according to claim 1, or pharmaceutically acceptable salt thereof, for treating NASH (non-alcoholic steatohepatitis), pulmonary fibrosis, chronic obstructive pulmonary disease (COPD), retinopathy or nephropathy in a patient in need thereof.

13. A pharmaceutical composition comprising a compound according to claim 1, or a pharmaceutically acceptable salt thereof, optionally together with one or more inert carriers and/or diluents.

14. A pharmaceutical composition comprising one or more compounds according to claim 1, or a pharmaceutically acceptable salt thereof, and one or more additional therapeutic agents, optionally together with one or more inert carriers and/or diluents.

15. The compound according to claim 9 having the structure

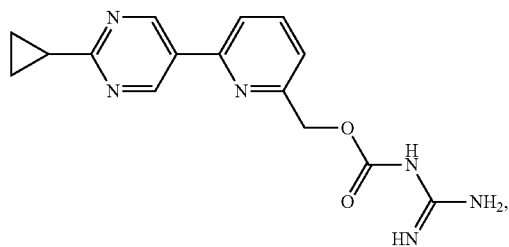 [SMILES: N=C(N)NC(=O)OCc1cccc(-c2cnc(C3CC3)nc2)n1]

or a salt thereof.

16. The compound according to claim 9 having the structure

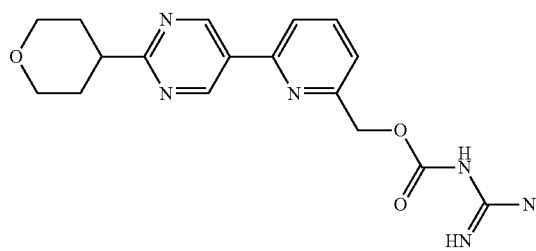

or a salt thereof.

17. The compound according to claim 9 having the structure

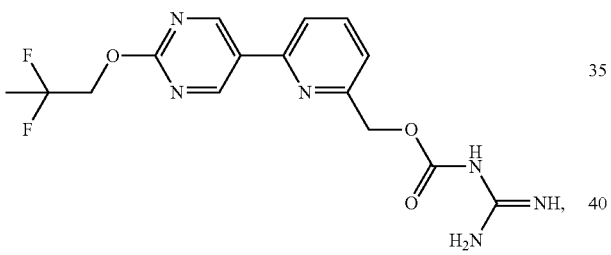

or a salt thereof.

18. The compound according to claim 9 having the structure

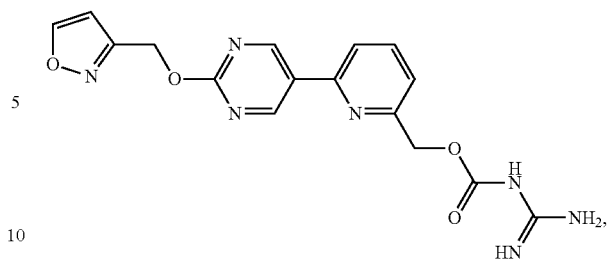

or a salt thereof.

19. The compound according to claim 9 having the structure

or a salt thereof.

20. The compound according to claim 9 having the structure

or a salt thereof.

21. The method according to claim 12, wherein the retinopathy is diabetic retinopathy.

* * * * *